United States Patent
Niyato et al.

(10) Patent No.: US 9,007,908 B2
(45) Date of Patent: Apr. 14, 2015

(54) SYSTEM AND METHOD FOR REMOTE AND MOBILE PATIENT MONITORING SERVICE USING HETEROGENEOUS WIRELESS ACCESS NETWORKS

(75) Inventors: Dusit Niyato, Nanyang View (SG); Abu Zafar Ekram Hossain, Winnipeg (CA); Sergio Guido Camorlinga, Winnipeg (CA)

(73) Assignee: Telecommunications Research Laboratories, Edmonton, Alberta (CA)

( * ) Notice: Subject to any disclaimer, the term of this patent is extended or adjusted under 35 U.S.C. 154(b) by 583 days.

(21) Appl. No.: 12/573,581

(22) Filed: Oct. 5, 2009

(65) Prior Publication Data

US 2010/0145161 A1 Jun. 10, 2010

Related U.S. Application Data

(60) Provisional application No. 61/102,667, filed on Oct. 3, 2008.

(51) Int. Cl.
*H04L 12/56* (2006.01)
*H04L 12/28* (2006.01)
(Continued)

(52) U.S. Cl.
CPC ........... *H04W 84/10* (2013.01); *G06F 19/3418* (2013.01); *H04W 88/06* (2013.01); *A61B 5/0022* (2013.01)

(58) Field of Classification Search
CPC ..... G06F 19/3418; H04L 67/12; H04L 1/002; H04W 88/06; H04W 64/00; H04W 72/1226; H04W 72/12; A61B 5/0002
USPC ................ 370/230, 395.21, 412, 235–395.2; 455/436, 439, 452.2, 450, 522, 437, 455/406, 458; 128/903, 904; 379/45, 230, 379/106.02; 702/118; 600/300, 323; 713/151; 607/60; 340/5.53, 870.01; 709/219, 221

See application file for complete search history.

(56) References Cited

U.S. PATENT DOCUMENTS 5,793,747 A * 8/1998 Kline ............................ 370/230
6,195,425 B1 * 2/2001 Farris ........................... 379/230

(Continued)

OTHER PUBLICATIONS

Fensli et al, "A Wireless ECG System for Continuous Event Recording and Communication to a Clinical Alarm Station", Proceedings of the 26th Annual International Conference of the IEEE EMBS, Sep. 1-5, 2004, pp. 2208-2211. (annotated copy attached to the office action).*

(Continued)

*Primary Examiner* — Wing F Chan
*Assistant Examiner* — Raji Krishnan
(74) *Attorney, Agent, or Firm* — J. Jay Haugen; Dentons Canada LLP

(57) ABSTRACT

A system and method for remote and mobile patient monitoring service is provided using heterogeneous wireless access in which each patient is equipped with a remote monitoring device with a heterogeneous wireless transceiver. This can be a value-added service provided by a Healthcare service provider (i.e., a hospital or healthcare center) for which the Healthcare service provider can pay to the wireless network service provider (i.e., a network operator). With heterogeneous wireless access, a remote/mobile patient can use different types of wireless technologies (e.g., WiMAX-based WMAN and WiFi-based WLAN technologies) to transfer monitored bio-signal data to the healthcare center. The monitoring device can buffer and then transmit the bio-signal data to the healthcare center through the heterogeneous radio access network. In this device, there can be two buffers used to store bio-signal data, each with different priority. The scheduler in this device can make an optimal decision on data transmission. Also, a method is provided to minimize the cost of network connections for remote/mobile patient monitoring.

24 Claims, 10 Drawing Sheets

(51) Int. Cl.
  H04W 84/10    (2009.01)
  G06F 19/00    (2011.01)
  A61B 5/00     (2006.01)
  H04W 88/06    (2009.01)

(56) References Cited

U.S. PATENT DOCUMENTS

| | | | |
|---|---|---|---|
| 6,385,302 B1* | 5/2002 | Antonucci et al. | 379/45 |
| 6,470,447 B1* | 10/2002 | Lambert et al. | 713/151 |
| 6,591,103 B1* | 7/2003 | Dunn et al. | 455/436 |
| 6,647,008 B1* | 11/2003 | Galand et al. | 370/389 |
| 6,760,310 B1* | 7/2004 | Sofman | 370/238 |
| 6,879,561 B1* | 4/2005 | Zhang et al. | 370/235 |
| 7,292,956 B1* | 11/2007 | Guday et al. | 702/118 |
| 2002/0194316 A1* | 12/2002 | Gous et al. | 709/221 |
| 2005/0286532 A1* | 12/2005 | Mengerink | 370/395.2 |
| 2007/0030116 A1* | 2/2007 | Feher | 340/5.53 |
| 2007/0067373 A1* | 3/2007 | Higgins et al. | 707/206 |
| 2008/0079566 A1* | 4/2008 | Singh et al. | 340/539.13 |
| 2008/0298389 A1* | 12/2008 | Nagaike | 370/468 |
| 2009/0062887 A1* | 3/2009 | Mass et al. | 607/60 |
| 2011/0294524 A1* | 12/2011 | Tontinuttananon et al. | 455/458 |
| 2013/0006899 A1* | 1/2013 | Cook | 706/12 |
| 2013/0218379 A1* | 8/2013 | Filev et al. | 701/22 |
| 2014/0005877 A1* | 1/2014 | Xu et al. | 701/29.1 |

OTHER PUBLICATIONS

Dejan V. Djonin and Vikram Krishnamurthy, "Structural Results on the Optimal Transmission Scheduling Policies and Costs for Correlated Sources and Channels" Proceedings of the 44th IEEE Conference on Decision and Control, and the European Control Conference 2005, Seville, Spain, Dec. 12-15, 2005.*

P. Kall and S. W. Wallace, Stochastic Programming, Wiley John & Sons, 1995, in its entirety.

E. Altman, Constrained Markov Decision Processes: Stochastic Modeling, Chapman & Hall/CRC, 1999, in its entirety.

M. L. Puterman, Markov Decision Processes: Discrete Stochastic Dynamic Programming, Wiley-Interscience, 1994, in its entirety.

R. S. Sutton and A. G. Barto, Reinforcement Learning: An Introduction (Adaptive Computation and Machine Learning), MIT Press, 1998, in its entirety.

Q. Song and A. Jamalipour, "A network selection mechanism for next generation networks," in Proc. IEEE International Conference on Communications (ICC), vol. 2, pp. 1418-1422, May 2005.

O. Ormond, J. Murphy, and G.-M. Muntean, "Utility-based intelligent network selection in beyond 3G systems," in Proc. IEEE International Conference on Communications (ICC), vol. 4, pp. 1831-1836, Jun. 2006.

W. Shen and Q.-A. Zeng, "Cost-function-based network selection strategy in integrated wireless and mobile networks," IEEE Trans. Veh. Technol., vol. 57 No. 6, pp. 3778-3788, Nov. 2008.

L.-C. Wang, A. Chen, and H.-H. Chen, "Network selection with joint vertical and horizontal handoff in heterogeneous WLAN and mobile WiMax systems," in Proc. IEEE Vehicular Technology Conference (VTC) Spring, pp. 794-798, Apr. 2007.

F. Bari and V. Leung, "Application of Electre to network selection in a heteroegeneous wireless network environment," in Proc. IEEE Wireless Communications and Networking Conference (WCNC), Mar. 2007.

D. Niyato and E. Hossain, "A noncooperative game-theoretic framework for radio resource management in 4G heterogeneous wireless access networks," IEEE Trans. Mobile Computing, vol. 7, No. 3, pp. 332-345, Mar. 2008.

K. Chebrolu and R. R. Rao, "Bandwidth aggregation for real-time applications in heterogeneous wireless networks," IEEE Transactions on Mobile Computing, vol. 5, No. 4, pp. 388-403, Apr. 2006.

G. T. Karetsos, S. A. Kyriazakos, E. Groustiotis, F. D. Giandomenico, and I. Mura, "A hierarchical radio resource management framework for integrating WLANs in cellular networking environments," IEEE Wireless Communications, vol. 12, No. 6, pp. 11-17, Dec. 2005.

F. Yu and V. Krishnamurthy, "Optimal joint session admission control in integrated WLAN and CDMA cellular networks with vertical handoff," IEEE Transactions on Mobile Computing, vol. 6, No. 1, pp. 126-139, Jan. 2007.

W. Song, H. Jiang, and W. Zhuang, "Performance analysis of the WLAN-first scheme in cellular/WLAN interworking," IEEE Transactions on Wireless Communications, vol. 6, No. 5, May 2007.

M. Bernaschi, F. Cacace, G. Iannello, S. Za, and A. Pescape, "Seamless internetworking of WLANs and cellular networks: Architecture and performance issues in a Mobile IPv6 scenario," IEEE Wireless Commun., vol. 12, No. 3, pp. 73-80, Jun. 2005.

N. Shenoy and R. Montalvo, "A framework for seamless roaming across cellular and wireless local area networks," IEEE Wireless Commun., vol. 12, No. 3, pp. 50-57, Jun. 2005.

E. S.-Navarro, Y. Lin, and V. W. S. Wong, "An MDP-based vertical handoff decision algorithm for heterogeneous wireless networks," IEEE Trans. Veh. Technol., vol. 57, No. 2, pp. 1243-1254, Mar. 2008.

V. S. Azhari, M. Smadi, and T. D. Todd, "Fast client-based connection recovery for soft WLAN-to-cellular vertical handoff," IEEE Trans. Veh. Technol., vol. 57, No. 2, pp. 1089-1102, Mar. 2008.

B. Boulanger, P. Kearney, J. Ochoa, B. Tsuei, and F. Sands, "Telemedicine: A solution to the followup of rural trauma patients," J. American College of Surgeons, vol. 192, No. 4, pp. 447-452, 2001.

R. Fensli, E. Gunnarson, and O. Hejlesen, "A wireless ECG system for continuous event recording and communication to a clinical alarm station," in Proc. International Conference of IEEE Engineering in Medicine and Biology Society (IEMBS), vol. 1, pp. 2208-2211, Sep. 2004.

C. H. Salvador, M. P. Carrasco, M. A. G. de Mingo, A. M. Carrero, J. M. Montes, L. S. Martin, M. A. Cavero, I. F. Lozano, and J. L. Monteagudo, "Airmed-cardio: A GSM and Internet services-based system for out-of-hospital follow-up of cardiac patients," IEEE Trans. Inform. Technol. Biomed., vol. 9, No. 1, pp. 73-85, Mar. 2005.

E. Guainella, E. Borcoci, M. Katz, P. Neves, M. Curado, F. Andreotti, and E. Angori, "WiMAX technology support for applications in environmental monitoring, fire prevention and telemedicine," in Proc. IEEE Mobile WiMAX Symposium, pp. 125-131, Mar. 2007.

D. Niyato, E. Hossain, and J. Diamond, "IEEE 802.16/WiMAX-based broadband wireless access and its application for telemedicine/eHealth services," IEEE Wireless Commun., vol. 14, No. 1, pp. 72-83, Feb. 2007.

S. D. Baker and D. H. Hoglund, "Medical-grade, mission-critical wireless networks," IEEE Eng. Med. Biol. Mag., vol. 27, No. 2, pp. 86-95, Mar.-Apr. 2008.

J. C. Tejero-Calado, C. Lopez-Casado, A. Bernal-Martin, M. A. Lopez-Gomez, M. A. Romero-Romero, G. Quesada, J. Lorca, and R. Rivas, "IEEE 802.11 ECG monitoring system," in Proc. International Conference of IEEE Engineering in Medicine and Biology Society (IEMBS), pp. 7139-7142, Jan. 2006.

Y.-H. Lin, I.-C. Jan, P. C.-I. Ko, Y.-Y. Chen, J.-M. Wong, and G.-J. Jan, "A wireless PDA-based physiological monitoring system for patient transport," IEEE Trans. Inform. Technol. Biomed., vol. 8, No. 4, pp. 439-447, Dec. 2004.

D. Niyato, E. Hossain, and J. Diamond, "Fourth generation heterogeneous wireless access networks for eHealth services: Architecture and radio resource management," Chapter 14 in Mobile Telemedicine: A Computing and Networking Perspective, Auerbach Publications, 2008, pp. 267-295.

D. Djonin, A. Karmokar, and V. Bhargava, "Joint rate and power adaptation for type-I hybrid ARQ systems over correlated fading channels under different buffer-cost constraints," IEEE Transactions on Vehicular Technology, vol. 57, No. 1, pp. 421-435, Jan. 2008.

* cited by examiner

SYSTEM AND METHOD FOR REMOTE AND MOBILE PATIENT MONITORING SERVICE USING HETEROGENEOUS WIRELESS ACCESS NETWORKS

CROSS REFERENCE TO RELATED APPLICATIONS

This application claims priority of U.S. provisional patent application Ser. No. 61/102,667 filed Oct. 3, 2008 and hereby incorporates the same provisional application by reference herein in its entirety.

TECHNICAL FIELD

The present disclosure is related to the field of eHealth wireless technologies, in particular, remote and mobile patient monitoring wireless technologies.

BACKGROUND eHealth (Electronic Health) is an emerging medical service paradigm, which employs information processing and communications to enhance traditional medical services. Remote patient monitoring is an eHealth service, which is used to monitor biosignal data of patients in a stable condition. The biosignal data of a remote/mobile patient can be transferred and processed for diagnosis (e.g., cardiac disease patients by monitoring electrocardiogram ("ECG") signal and blood pressure or diabetes patients by monitoring sugar level). Remote patient monitoring services can reduce the frequency of face-to-face meetings between patients and healthcare staff and also shorten the time required for treatment acceptance and better management of medication doses to patients. Wireless technologies have been used to improve the flexibility of remote patient monitoring to continuously monitor the status of patients even in presence of mobility. Related works on heterogeneous wireless networks and remote patient monitoring systems can be summarized as follows.

A. Heterogeneous Wireless Networks

Network selection is one of the major issues in heterogeneous wireless access [3]-[7]. The decision on network selection by a mobile user depends on the preference, application requirements, and network condition [3]. An intelligent network selection algorithm based on user utility was proposed in [4]. This user utility is a function of the transmission rate, and different applications can have different utility functions. The network selection algorithm in [5] took both network performance and network access cost into account. In [8], the problem of radio resource allocation for different service providers in a heterogeneous wireless environment was formulated as a noncooperative game and the solution was obtained in terms of allocated bandwidth in different service areas. In [9], a bandwidth aggregation scheme for real-time applications in heterogeneous wireless network was proposed. This scheme uses the earliest delivery path first (EDPF) scheduling to choose packets from different applications to be transmitted over multiple wireless interfaces so that the delay requirements are satisfied. In [10], to alleviate network congestion, a hierarchical radio resource management framework was designed for an integrated wireless local area network ("WLAN") and cellular network.

Since mobile users need to be handed over between different types of networks (i.e., vertical handoff) mobility management is a significant issue in a heterogeneous wireless access environment [11]-[16]. The problem of admission control for vertical handoff in an integrated WLAN and code division multiple access ("CDMA") cellular network was proposed in [11] where an optimization problem was formulated as a Markov decision process to minimize call blocking probability while satisfying the throughput and packet delay requirements. In [12], a performance analysis model was proposed for vertical handoff an integrated cellular network and WLAN.

B. eHealth Services Using Wireless Communications

For patients with cardiac diseases, ECG signal can be monitored and transmitted wirelessly to the healthcare center [17]-[19]. GSM (Global System for Mobile Communication) technology and wireless application protocol (WAP) were used in the airmed-cardio system [19] to provide out-of-hospital follow-up services to cardiac patients. Although a cellular network can provide wireless connectivity to highly-mobile patients, its capacity is limited. Besides cellular technology, new wireless technologies (e.g., IEEE 802.16-based (also known as Worldwide Interoperability for Microwave Access ("WiMAX")) wireless metropolitan area network ("WMAN") and IEEE 802.11/WiFi-based wireless local area network ("WLAN")) are also adopted for remote patient monitoring services [20]-[24]. In [21], application of IEEE 802.16/WiMAX-based broadband wireless access technology for mobile telemedicine services (e.g., communication between an ambulance and hospital) was discussed. Also, in [21], a bandwidth allocation and admission control scheme was designed specifically for telemedicine services over a WiMAX network. WiFi technology, which provides large transmission capacity in a small coverage area, can be used locally in a hospital, clinic, and home environment for patient monitoring, clinical alarm notification, workstation on wheels [22], ECG monitoring [23], and telehomecare. Also, WiFi networks are suitable to provide best-effort data communication services for commercial and support applications (e.g., guest access and patient billing [22]).

The concept of using heterogeneous wireless access networks for remote monitoring service was introduced in [25], where a general system model was presented for different eHealth services (e.g., intra-hospital, pre-hospital, telehomecare, and follow-up services) based on heterogeneous wireless access. Also, a bandwidth allocation and admission control method was developed based on resource sharing using game theory. However, optimization of capacity reservation in the radio access network and issues related to queue management and transmission scheduling in a patient-attached device were not considered.

However, since the traditional remote patient monitoring systems rely on a single wireless technology, they are unable to guarantee that the patients will be "always-connected" with the eHealth service provider (e.g., healthcare center) when the patient roams through different locations.

It is, therefore, desirable to provide a patient monitoring system that implements wireless technologies to enable continuous and ubiquitous patient monitoring wherever and whenever the patient needs.

SUMMARY

An architecture of a remote/mobile patient monitoring service based on the heterogeneous wireless access is provided. eHealth service providers can provide such a value-added service to guarantee the "always-connected" feature "anytime, anywhere" to the patients. The eHealth service provider can be connected with the core network of the wireless network operator. This core network can be connected with any one of the different radio access networks (i.e., IEEE 802.16-based WMAN and IEEE 802.11-based WLAN). A patient-attached device can be employed at or placed on the patient to buffer and control the transmission of biosignal data from sensors on the patient to the radio access network. The biosignal data with different priority can be differentiated by storing the data in the different queues whereby the scheduler can decide to retrieve and transmit data from these different queues according to quality-of-service ("QoS") requirements. A method to optimize the cost and performance of this remote/mobile patient monitoring service is also provided.

Broadly stated, a system is provided for the remote and mobile monitoring of at least one patient, comprising: a heterogeneous wireless access network providing communication between at least one eHealth service provider and the at least one patient; and at least one monitoring device disposed on the at least one patient, the at least one monitoring device having at least one sensor configured for collecting bio-signal data from the at least one patient, the at least one monitoring device further comprises a heterogeneous wireless transceiver configured to communicate the bio-signal data to the eHealth service provider over the heterogeneous wireless access network.

Broadly stated, a method is provided for buffering and transmitting bio-signal data from a patient-attached monitoring device to an eHealth service provider over a heterogeneous wireless access network, the method comprising the steps of: providing a heterogeneous wireless access network providing communication between at least one eHealth service provider and at least one patient; providing at least one monitoring device and attaching the at least one monitoring device to the at least one patient, the at least one monitoring device having at least one sensor configured for collecting bio-signal data from the at least one patient, the bio-signal data comprising one or more of the group consisting of critical data and normal data, the at least one monitoring device further comprising a heterogeneous wireless transceiver configured to communicate the bio-signal data to the eHealth service provider over the heterogeneous wireless access network; receiving bio-signal data from the at least one monitoring device, the bio-signal data collected by the at least one monitoring device from the at least one patient; packeting and buffering the bio-signal data into at least one queue; and connecting the at least one queue to the heterogeneous wireless transceiver and transmitting the bio-signal data to the eHealth service provider over the heterogeneous wireless access network.

Broadly stated, a system is provided for buffering and transmitting bio-signal data from a patient-attached monitoring device to an eHealth service provider over a heterogeneous wireless access network, comprising: collection means for collecting bio-signal data from the at least one patient, the bio-signal data comprising one or more of the group consisting of critical data and normal data; communications means for communicating the bio-signal data to the eHealth service provider over the heterogeneous wireless access network; means for receiving bio-signal data from the collection means; means for packeting and buffering the bio-signal data into at least one queue; and means for connecting the at least one queue to the communications means and transmitting the bio-signal data to the eHealth service provider over the heterogeneous wireless access network.

DETAILED DESCRIPTION OF EMBODIMENTS

Figure 1A:
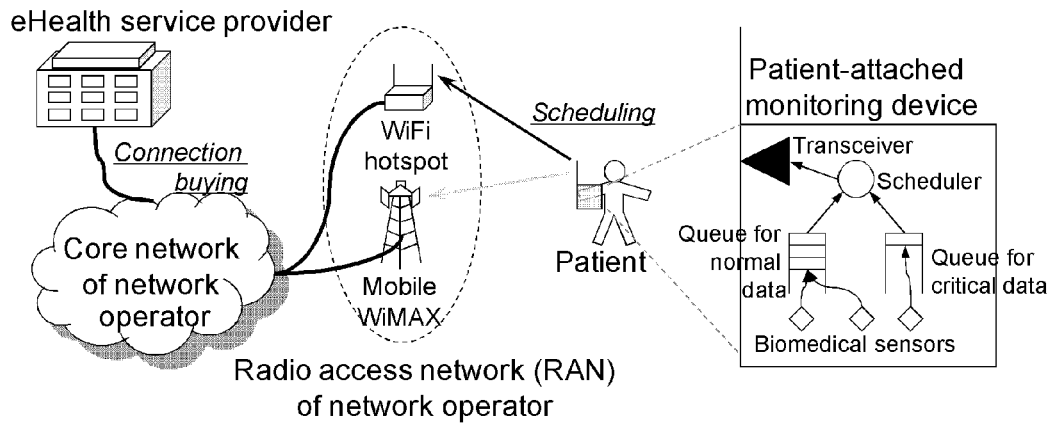
FIG. 1(a) is a block diagram depicting a system model of a remote patient monitoring system.

To support biosignal data collection, a general network model for the remote patient monitoring service is shown in FIG. 1(a). The two major entities in this network are the healthcare service provider (e.g., clinic, hospital, or healthcare center) and the network service provider (or network operator). Monitored biosignal data from the patients can be transferred through a radio access network and core network owned by the network service provider to the healthcare service provider. The remote monitoring device can be connected with the sensors attached to a chronic patient whose health condition is stable, for example, a patient with hypertension or with cardiac diseases. The monitored data can be packetized and buffered into the queues based on the priority. In one embodiment, there can be two types of queues in this device—one for critical data (e.g., blood pressure, pulse rate, heart rate) and the other for normal data (e.g., ECG signal). The scheduler can connect the queues for critical and normal data with the heterogeneous wireless transceiver that can dynamically adapt and connect to the healthcare service provider by using an available wireless network.

In one embodiment, a remote and mobile patient monitoring service architecture can use heterogeneous wireless access in which each patient can be equipped with a remote monitoring device with a heterogeneous wireless transceiver (FIG. 1(a)). With heterogeneous wireless access, a mobile patient can use different types of wireless technologies (e.g., WiMAXbased WMAN and WiFi-based WLAN technologies) to transfer monitored biosignal data to the healthcare center. The monitoring device can buffer and then transmit the biosignal data to the healthcare center through the heterogeneous radio access network. This is a value-added service that can be provided by an eHealth service provider (i.e., a hospital or healthcare center) for which the eHealth service provider can pay the wireless network service provider (i.e., a network operator). To optimize the cost for this value-added service, the eHealth service provider has to buy a certain number of connections to be reserved for the patients. This can be formulated as an optimization problem and can be solved using a stochastic programming technique [1] so that the optimal number of reserved connections can be determined to minimize the cost of the eHealth service provider under randomness of connection demand due to the mobility of the patients.

Figure 1B:
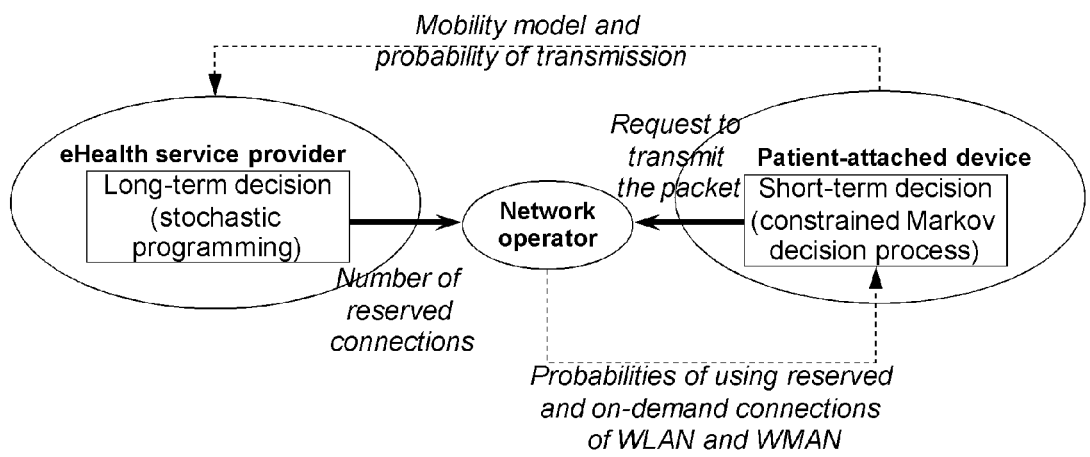
FIG. 1(b) is a block diagram depicting the decision flowchart of the remote patient monitoring system of FIG. 1(a).

While the eHealth service provider buys the reserved wireless connections for its patients on a long-term basis, the patient-attached monitoring device has to schedule the transmission of biosignal data according to the current network condition on a short-term basis (FIG. 1(b)). Since different queues can be used to buffer different types of biosignal data (i.e., critical and normal monitored data), the scheduler at the patient-attached device has to decide whether to transmit data using the available wireless connections, as well as the queue from which data is to be transmitted. This decision problem at the scheduler can be formulated as a constrained Markov decision process ("CMDP") [2] with an objective to minimizing the cost of wireless access while satisfying the queueing delay requirements for different biosignal data. However, to obtain the optimal policy for the CMDP model, a linear programming problem needs to be solved which incurs large computational complexity. Therefore, an implementation-friendly algorithm based on Q-learning can be implemented to obtain the solution online. The performance of the remote patient monitoring service architecture can be extensively evaluated. The proposed architecture along with the optimization formulation can be useful for an eHealth service provider to minimize the service cost while maintaining the quality-of-service (QoS) requirements for remote and mobile patient monitoring.

In one embodiment, the system model and optimization formulation presented herein can be used for many eHealth services. In another embodiment, the system and method can be used in the monitoring of ECG signals for patients with cardiac diseases. The ECG signal can be sampled by an ECG device/sensor. The data can then be packetized and stored in a queue as "normal" data waiting for transmission over wireless connections. However, if an abnormal event is detected (e.g., heart rate becomes too low), a special message with the detailed information of the event (e.g., location, time, and condition of the patient) can be generated and stored in a separate queue as "critical" data. In this case, priority can be given to the transmission of "critical" data, so that the patient can be treated promptly. The rest of this application is organized as follows. The architecture of the remote patient monitoring service is described in Section I. Section II presents the optimization formulations to minimize the cost of the proposed remote patient monitoring service. Section III presents the performance evaluation results. Conclusions are stated in Section IV.

I. ARCHITECTURE OF REMOTE PATIENT MONITORING SERVICE USING HETEROGENEOUS WIRELESS ACCESS

A. Network Model

To support biosignal data collection, a general network model for the remote patient monitoring service is shown in FIG. 1(a). Two major entities in this network are the eHealth service provider (e.g., clinic, hospital, or healthcare center) and the network service provider (or network operator). Monitored biosignal data from the patients can be transferred through a radio access network and core network owned by the network service provider to the eHealth service provider. The network operator can offer two types of wireless connections, namely, reserved and on-demand connections. In particular, the eHealth service provider can buy the reserved connections in advance to be used by its patients for a fixed period of time (e.g., a week). However, at a particular time, the reserved connections may not be enough to accommodate all demand from the patients for transmitting biosignal data. Therefore, extra network capacity (i.e., on-demand connections in this case) can be bought for the exceeding demand. The price of an on-demand connection is assumed to be higher than that of a reserved connection.

In one embodiment, a service area can comprise a set of locations. For example, in the service area shown in FIG. 2(a), wireless access to WMAN and WLAN are available (e.g., IEEE 802.16 and IEEE 802.11). While WLAN access is available only in some locations, WMAN access can be available in all locations of a service area. Remote and mobile patients can connect to either a WLAN or the WMAN. The prices charged for a reserved connection and an on-demand WLAN connection at location l are denoted by $P_{res,l}^{wl}$ and $P_{ond,l}^{wl}$ respectively, and the prices for the WMAN connections are denoted by $P_{res,l}^{wm}$ and $P_{ond,l}^{wm}$. It is assumed that $P_{res,l}^{wl} \leq P_{ond,l}^{wl}$ and $P_{res,l}^{wm} \leq P_{ond,l}^{wm}$.

B. Patient-Attached Monitoring Device

The remote monitoring device can be connected with the sensors attached to a patient whose health condition is stable, for example, a patient with hypertension or with cardiac diseases (FIG. 1(a)). The monitored data can be packetized and, based on its priority, it can be buffered in one of the two queues—one for critical data (e.g., blood pressure, pulse rate, heart rate) and the other for normal data (e.g., ECG signal). The scheduler can connect to the queues for critical and normal data with the heterogeneous wireless transceiver. To minimize the connection cost and satisfy the delay requirements, the scheduler can make two decisions—1) whether to transmit data or not and, in the case of transmission, 2) which queue to transmit from. The duration of a transmission slot can be assumed to be fixed during which one packet can be transmitted. This transmission slot can be composed of the negotiation period between a device and a WMAN base station or WLAN access point, and the data transmission period.

C. Patient Mobility Model

In another embodiment, a patient can move among different locations with different availability of wireless access networks. A set of locations in a service area is denoted by L. For example, in FIG. 2(a), this set can be defined as follows: L={Ma, Ro, Cl, Ho} whose elements represent the mall, road, clinic, and home, respectively. At the mall and a clinic, a patient can have access to both WLAN and WMAN. While traveling on the road, only WMAN connectivity can be available. Given a set of locations in a service area, the mobility of a patient can be modeled by using a Markov chain. The state of this Markov chain can be the location that is observed at the end of a transmission slot. The transition from location l to l' is indicated by probability $T_{l,l'}$, and the probability transition matrix is denoted by T. The steady-state probability that a patient will be in any location can be obtained by solving $\pi T = \pi$ and $\pi 1 = 1$ where 1 is a vector of ones, $\pi$ is a vector defined as follows: $\pi = [\ldots \pi(l) \ldots]$, in which $\pi(l)$ is the steady-state probability that a patient will be at location l.

II. OPTIMIZATION OF WIRELESS CONNECTIVITY COST FOR PATIENT MONITORING SERVICE

In one embodiment, an optimization problem for the eHealth service provider to buy the reserved connections from the network operator can be formulated as a stochastic programming ("SP") problem. The solution of this SP can give the number of reserved connections at a particular location, which can minimize the expected cost of network access under uncertainty of the number of patients in different locations in a service area. Another optimization problem based on a CMDP can be formulated for the patient-attached monitoring device to schedule packet transmissions so that the delay requirements for different biosignal data are satisfied while, at the same time, the network access cost can also minimized. Therefore, both of these optimization models together can improve the efficiency of the proposed remote monitoring service architecture.

A. Optimization of Connection Buying by eHealth Service Provider

1) Probability Distribution of Patients in Different Locations:

In one embodiment, $N_p$ can denote the total number of patients in a service area A, and $T_i$ can denote the mobility transition probability matrix of patient i. The mobility transition probability matrix for all patients $T_A$ in service area A can be obtained from:

$$T_A = T_1 \otimes \ldots \otimes T_i \otimes \ldots \otimes T_{N_p} \quad (1)$$

where $\otimes$ denotes Kronecker product.

The steady-state probability of a patient to be at a particular location can be obtained by solving $\pi T_A = \pi$ and $\pi 1 = 1$. In this case, the steady-state probability for patient i at location $l_i$ is denoted by $\pi(l_1, \ldots, l_i, \ldots, l_{N_p})$. Then, the probability of having $n_l$ patients at a location l can be obtained from:

$$Pr(\ldots, n_l, \ldots) = \sum_{n_l = \sum_{l_i = l} 1} \pi(l_1, \ldots, l_i, \ldots, l_{N_p}) \quad (2)$$

for $\sum_{l \in L} n_l = N_p$.

Note that the term $$\sum_{l_i = l} 1$$

above indicates the number of patients at location l. For the special case of all patients having the same $\pi$, the probability of having $n_l$ patients at location l can be simply obtained based on a multinomial distribution.

2) Formulation of Stochastic Programming:

In another embodiment, a two-stage stochastic programming (SP) with recourse [1] can be used to obtain the number of reserved connections in WLAN and WMAN in a service area. In the first stage, the eHealth service provider can make a decision on the number of reserved connections to be bought from a network operator. The decision in this stage has to be made without complete information on the random number of patients in each location requesting to transmit biosignal data. The number of reserved connections to be bought at location l for accessing WLAN and WMAN is denoted by $x_l^{wl}$ and $x_l^{wm}$, respectively. In the second stage, the eHealth service provider can observe the actual number of patients in a particular location (i.e., realization) and makes a decision to buy on-demand connections if the number of patients is larger than the number of available reserved connections. The number of on-demand connections to be bought at location l for accessing WLAN and WMAN are denoted by $y_l^{wl}$ and $y_l^{wm}$, respectively. The decision in the second stage (i.e., $y_l^{wl}$ and $y_l^{wm}$) can be referred to as a recourse, which is an action used to handle the uncertainty arising due to the mobility of the patients.

The SP problem can be formulated as follows:

$$\text{Minimize} \sum_{l \in L_{wl}} P_{res,l}^{wl} x_l^{wl} + \sum_{l \in L_{wm}} P_{res,l}^{wm} x_l^{wm} + E_\omega \mathcal{Z}(x, \omega) \quad (3)$$

$$\text{Subject to: } x_l^{wl} + y_l^{wl}(\omega) \geq \hat{n}_l(\omega), \text{ for } l \in L_{wl} \quad (4)$$

$$x_l^{wm} + y_l^{wm}(\omega) \geq \hat{n}_l(\omega), \text{ for } l \in L_{wm} \quad (5)$$

$$x_l^{wl}, x_l^{wm}, y_l^{wl}, y_l^{wm} \geq 0 \quad (6)$$

where $L_{wl}$ and $L_{wm}$ denote, respectively, the sets of locations in which only WMAN access or only WLAN access is available (i.e., $L_{wl} \cup L_{wm} = L$) and $\omega = (\ldots, n_l, \ldots)$ for $l \in L$ (i.e., $\omega$ represents a network access scenario). $E_\omega$ denotes the expectation over all scenarios. In this case, the number of patients $\hat{n}_l$ requesting to transmit data at location l is a function of $\omega$, i.e., $\hat{n}_l(\omega) = v_l n_l$ where $v_l$ is the probability that a patient in location l will transmit data. The constraints in (4) and (5) are used to ensure that all requesting patients can transmit data through either reserved or on-demand connections. Note that the condition "≥" is required for the constraints in (4) and (5), since the decision $x_l^{wl}$ and $x_l^{wm}$ could be larger than the number of patients $\hat{n}_l(\omega)$. Therefore, the condition of equality may not be satisfied without making $y_l^{wl}(\omega)$ and $y_l^{wm}(\omega)$ negative which will violate the constraint in (6).

The objective defined in (3) has two parts—the cost incurred in the first stage for the reserved connections (i.e., $$\sum_{l \in L_{wl}} P_{res,l}^{wl} x_l^{wl} + \sum_{l \in L_{wm}} P_{res,l}^{wm} x_l^{wm}$$

and the cost incurred in the second stage due to buying extra on-demand connections, which can be referred to as the recourse cost (i.e., $E_\omega \mathcal{Z}(x, \omega)$). This expected recourse cost can be obtained from:

$$E_\omega \mathcal{Z}(x, \omega) = \sum_\omega Pr(\omega)(y_l^{wl} P_{ond,l}^{wl} + y_l^{wm} P_{ond,l}^{wm}) \quad (7)$$

The optimization formulation in (3)-(6) and (7) can be solved by using integer linear programming. Then, the average total cost for the eHealth service provider can be obtained as in (8).

$$ATC = \sum_\omega Pr(\ldots, n_l, \ldots) \quad (8)$$

$$\left( \sum_{l \in L} \sum_{j \in \{wl, wm\}} x_l^j P_{res,l}^j + \sum_{l \in L} \sum_{j \in \{wl, wm\}} \max(0, \hat{n}_l - x_l^j) P_{ond,l}^j \right)$$

B. Optimization of Transmission Scheduling at Patient-Attached Monitoring Device In another embodiment, the decisions on transmission scheduling can be made based on the number of reserved connections in each location which is a solution of the SP formulation described above. The patient-attached device can take the queue state and location into account when making a decision. The problem of optimal decision-making can be formulated as a CMDP to minimize the cost while the delay requirements for transmission of biosignal data are satisfied. The modeling assumptions, the problem formulation, and the solution approach for the CMDP are described below.

1) Packet Arrival Process:

In one embodiment, the packet arrival processes of critical and normal data can be modeled as a Markovian arrival process (MAP) which can be represented by matrices $A_c(a)$ and $A_n(a)$ for $a \in \{0,1\}$ packet arrivals corresponding to critical and normal data. This matrix can be defined as follows:

$$A(a) = \begin{bmatrix} A_{1,1}(a) & A_{1,2}(a) & \ldots & A_{1,K}(a) \\ \vdots & & & \vdots \\ A_{K,1}(a) & A_{K,2}(a) & \ldots & A_{K,K}(a) \end{bmatrix} \quad (9)$$

where $A_{k,k'}(a)$ is the probability that the arrival phase changes from k to k' and a packets arrive. K is the total number of phases of this MAP. To obtain the average arrival rate $\lambda$, the steady-state probability of the arrival process $\delta$ can be obtained from solving $\delta(A(0)+A(1))=\delta$ and $\delta 1=1$. The average packet arrival rate is obtained from:

$$\lambda = \delta A(1) 1 \quad (10)$$

2) Constrained Markov Decision Process Formulation:

The formulation of CMDP can be defined by a state space, a set of actions/control, a set of constraints, and cost. The state space can be expressed as in (11):

$$\Omega = \{(X_n, A_n, X_c, A_c, L, C); 0 \leq X_n \leq B_n, 0 \leq X_c \leq B_c, L \in L, C \in W\} \quad (11)$$

where $B_n$ and $B_c$ denote the queue sizes corresponding to critical data and normal data, $X_c$ and $X_n$ denote the number of packets in the queues, and $A_c$ and $A_n$ denote the phases of packet arrivals for critical and normal data, respectively. L denotes the location and C denotes the wireless connections available to the patient. The set of available wireless connections is defined as:

$$W = \{\text{reserved WLAN, on-demand WLAN, reserved WMAN, on-demand WMAN}\} \quad (12)$$

Figure 2A:
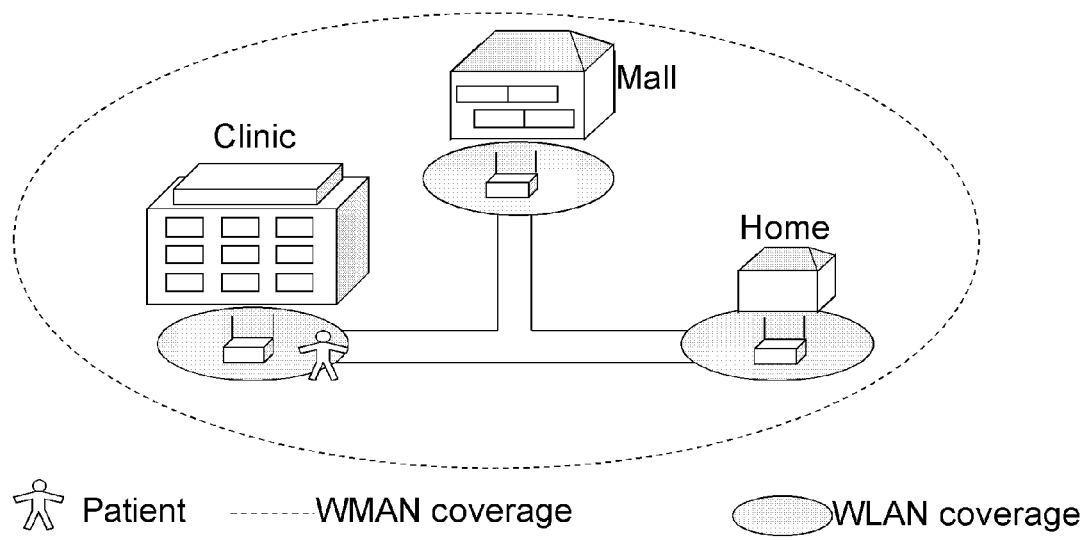
FIG. 2(a) is a block diagram depicting a sample service area for the remote patient monitoring system of FIG. 1(a).
Figure 2B:
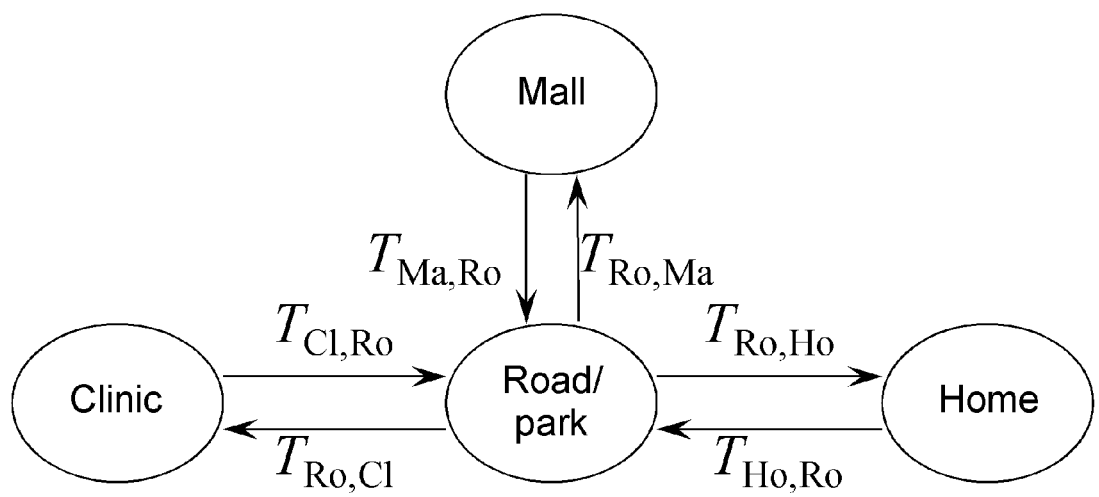
FIG. 2(b) is a block diagram depicting a mobility state transition diagram for the sample service area of FIG. 2(a).
Figure 3:
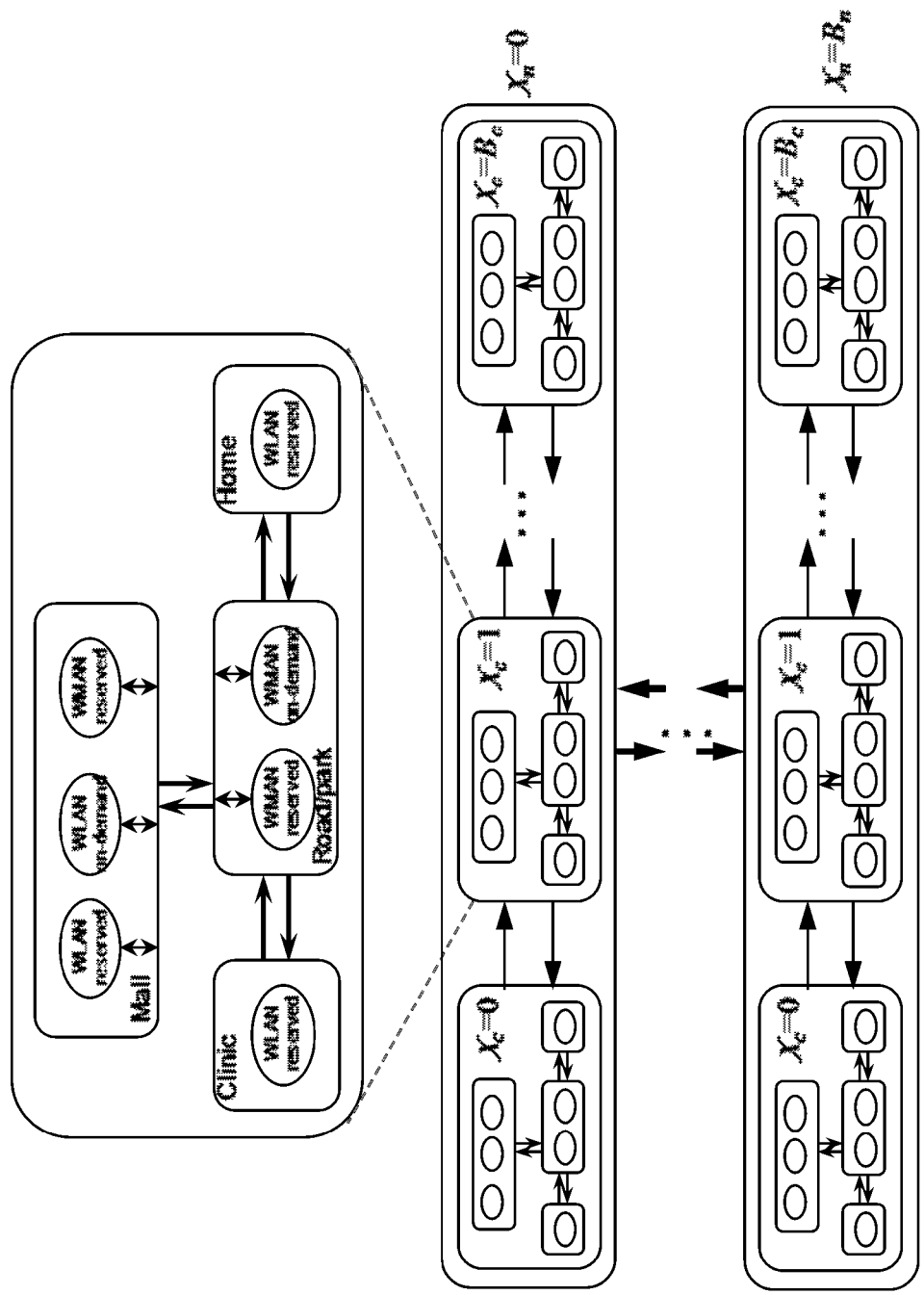
FIG. 3 is a block diagram depicting the state transitions for a Markov decision process model for the sample service area of FIG. 2(a).

For the service area in FIG. 2, the transitions among the states defined in $\Omega$ are shown in FIG. 3. In this embodiment, at the mall, there can be three available wireless connections, i.e., reserved WLAN, on-demand WLAN, and reserved WMAN. Since we assume that $P_{ond,l}^{wl} < P_{ond,l}^{wm}$, on-demand WLAN connection can be used instead of an on-demand WMAN connection.

The set of feasible actions at a composite state s can be defined as $U_s \subset \{1, 2, 3\}$, which corresponds to transmission of critical data, transmission of normal data, and no transmission, respectively. In this case, the transition probability matrix for states in $\Omega$ will be different due to the different actions. For a patient at location $l \in L_{wl}$ we first obtain the probabilities of transmitting data using reserved and on-demand connections in WLAN and WMAN. The type of connection (i.e., reserved or on-demand) and the target network (i.e., WLAN or WMAN) for transmission from each patient can be assigned by the network operator given the total number of requesting patients in a location. The low-cost reserved connections can be used first, while the on-demand connections will be used only when reserved connections are inadequate to accommodate all requesting patients.

Figure 4:
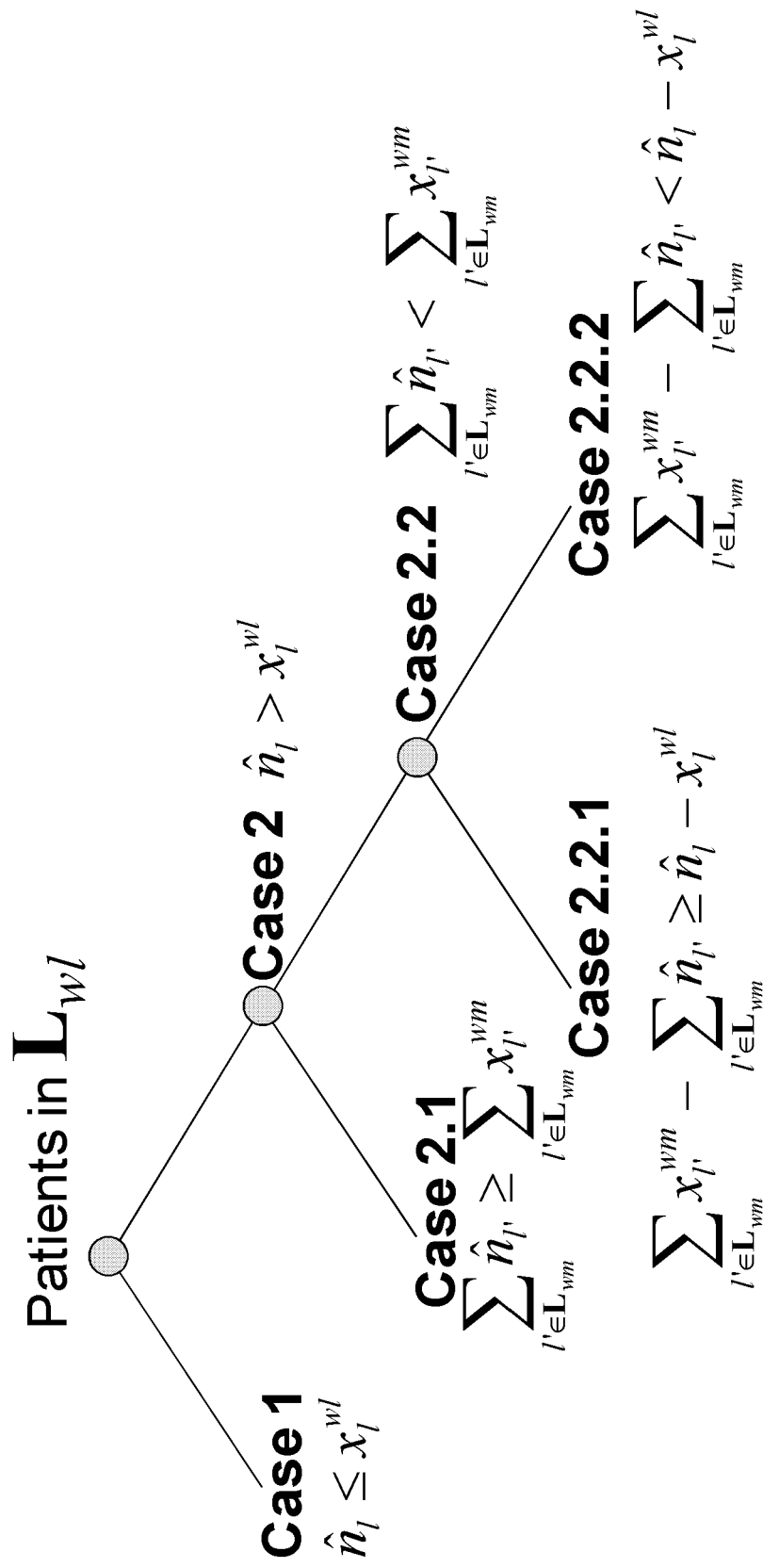
FIG. 4 is a line diagram depicting the cases of connections of patients.

For patients in location $l \in L_{wl}$, the cases that need to be considered are as follows (FIG. 4):

Case 1 ($\hat{n}_l \leq x_l^{wl}$ for $l \in L_{wl}$): In this case, the number of patients requesting to transmit data at location l can be smaller than or equal to the number of reserved WLAN connections. Therefore, all the patients can transmit using the reserved WLAN connections. The probability of using a reserved connection is $\rho_{res,l}^{wl}=1$.

Case 2 ($\hat{n}_l > x_l^{wl}$ for $l \in L_{wl}$): In this case, the number of patients requesting to transmit data at location l can be larger than the number of reserved WLAN connections. Therefore, some patients can use reserved WMAN connections (if available) or on-demand WLAN connections for transmitting data. The corresponding two cases are as follows:

Case 2.1 $\left( \sum_{l' \in L_{wm}} \hat{n}_{l'} \geq \sum_{l' \in L_{wm}} x_{l'}^{wm} \right)$:

In this case, the number of patients in locations $l' \in L_{wm}$, where only WMAN access is available, can be larger than or equal to the number of reserved WMAN connections. Therefore, some patients at location l will have to use reserved or on-demand WLAN connections. The probabilities of using reserved and on-demand WLAN connections are given, respectively, by $$\rho_{res,l}^{wl} = \frac{x_l^{wl}}{\hat{n}_l} \text{ and } \rho_{ond,l}^{wl} = \frac{\hat{n}_l - x_l^{wl}}{\hat{n}_l}.$$

Case 2.2 ($\sum_{l' \in L_{wm}} \hat{n}_{l'} < \sum_{l' \in L_{wm}} x_{l'}^{wm}$): In this case, the number of patients in locations where only WMAN access is available, can be smaller than the number of reserved WMAN connections. As a result, some of the additional patients at location l can use reserved WMAN connections. However, there are two corresponding cases as follows:

Case 2.2.1 $\left( \sum_{l' \in L_{wm}} x_{l'}^{wm} - \sum_{l' \in L_{wm}} \hat{n}_{l'} \geq \hat{n}_l - x_l^{wl} \right)$:

In this case, the number of available reserved WMAN connections can be larger than or equal to the number of additional patients at location l. Therefore, all additional patients at location l can use the reserved WMAN connections. The probabilities of using reserved WLAN and WMAN connections are given by:

$$\rho_{res,l}^{wl} = \frac{x_l^{wl}}{\hat{n}_l} \text{ and } \rho_{res,l}^{wm} = \frac{\hat{n}_l - x_l^{wl}}{\hat{n}_l}.$$

Case 2.2.2 $\left( \sum_{l' \in L_{wm}} x_{l'}^{wm} - \sum_{l' \in L_{wm}} \hat{n}_{l'} < \hat{n}_l - x_l^{wl} \right)$:

In this case, the number of available reserved WMAN connections can be smaller than the number of additional patients at location l. Therefore, some of the patients at location l will use the reserved WMAN connections or on-demand WLAN connections. The probabilities of using reserved and on-demand connections in WLAN and WMAN are given by:

$$\rho_{res,l}^{wl} = \frac{x_l^{wl}}{\hat{n}_l},$$

$$\rho_{ond,l}^{wl} = \frac{\hat{n}_l - x_l^{wl} - \left(\sum_{l' \in L_{wm}} x_{l'}^{wm} - \sum_{l' \in L_{wm}} \hat{n}_{l'}\right)}{\hat{n}_l}, \text{ and}$$

$$\rho_{res,l}^{wm} = \frac{\sum_{l' \in L_{wm}} x_{l'}^{wm} - \sum_{l' \in L_{wm}} \hat{n}_{l'}}{\hat{n}_l}.$$

Then, for a patient at a location where only WMAN access is available, the probability of using reserved and on-demand WMAN connections can be obtained. For patients in location $l \in L_{wm}$, there are two cases as follows:

Case 1 $\left(\sum_{l \in L_{wm}} \hat{n}_l \leq \sum_{l \in L_{wm}} x_l^{wm}\right)$:

This corresponds to the case that the number of requesting patients to transmit data is smaller than or equal to the number of reserved WMAN connections. Therefore, all patients can use the reserved connections. The probability of using a reserved WMAN connection is $\kappa_{res,l}^{wm} = 1$.

Case 2 $\left(\sum_{l \in L_{wm}} \hat{n}_l > \sum_{l \in L_{wm}} x_l^{wm}\right)$:

Some patients can use on-demand WMAN connections. The probabilities of using reserved and on-demand connections in a WMAN are given by:

$$\kappa_{res,l}^{wm} = \frac{\sum_{l \in L_{wm}} x_l^{wm}}{\hat{n}_l} \text{ and } \kappa_{ond,l}^{wm} = \frac{\sum_{l \in L_{wm}} \hat{n}_l - \sum_{l \in L_{wm}} x_l^{wm}}{\hat{n}_l}.$$

Let $c_l$ denote a vector of probability of connection availability at location l which can be defined as follows:

$$c_l = \begin{cases} [\rho_{res,l}^{wl}\ \rho_{ond,l}^{wl}\ \rho_{res,l}^{wm}] & l \in L_{wi} \\ [\kappa_{res,l}^{wm}\ \kappa_{ond,l}^{wm}] & l \in L_{wm}, \end{cases} \quad (13)$$

The transition matrix L combining the state transitions of location and connection availability (i.e., L and C) can be constructed based on the mobility transition matrix of a patient T with elements $T_{l,l'}$. The elements in transition matrix L are denoted by $L_{l,l'}$, which can be obtained from:

$$\check{L}_{l,l'} = \begin{cases} T_{l,l'}I, & l = l' \\ T_{l,l'}1^T c_{l'}, & l \neq l' \end{cases} \quad (14)$$

where I is an identity matrix.

Next, the state transitions for the packets in queue for critical data and phase of arrival process (i.e., $X_c$ and $A_c$) can be combined with those of location and available of connections. There are two cases corresponding to action $u \in U_s$. First, the case of action u=1 (i.e., a packet is retrieved from the queue for critical data for transmission) is considered.

Let $\beta_{res,l}^{wl}$, $\beta_{ond,l}^{wl}$, $\beta_{res,l}^{wm}$, $\beta_{ond,l}^{wm}$ denote the probabilities of successful transmission using reserved and on-demand WLAN and WMAN connections at location l. The location- and connection-dependent departure process for the packets in a queue can be represented in a matrix D(d) (i.e., d packet departs where $d \in \{0,1\}$). The elements of this matrix are denoted by $D_{l,l}(d)$ and can be obtained as follows:

$$\check{D}_{l,l'}(1) = \begin{cases} \begin{bmatrix} \beta_{res,l}^{wl} & & \\ & \beta_{ond,l}^{wl} & \\ & & \beta_{res,l}^{wm} \end{bmatrix}, & l = l' \in L_{wl} \\ \begin{bmatrix} \beta_{res,l}^{wm} & \\ & \beta_{ond,l}^{wm} \end{bmatrix} & l = l' \in L_{wm} \\ 0, & \text{otherwise} \end{cases}$$

$$\check{D}_{l,l}(0) = I - \check{D}_{l,l}(1) \quad (15)$$

where 0 is a matrix of zeros. Note that the size of matrix $D_c$ is the same as that of L.

Let Q(u=1) denote the transition matrix for action u=1 with elements denoted by $Q_{q,q'}(u)$ where the number of packets in the queue for critical data changes from q to q' for $q,q' \in \{0, 1, \ldots, B_c\}$. This can be obtained as in (16). For actions u=2,3 (i.e., the patient-attached device will transmit normal data or not transmit any data, respectively), no packet is retrieved from the queue for critical data. The derivation of the transition matrix Q(u=2,3) is similar to that of Q(u=1). However, the departure probability matrices become D(0)=I and D(1)=0, since no packet from the queue for critical data is transmitted.

Next, the state transitions for the packets in queue for normal data and phase of arrival process (i.e., $X_n$ and $A_n$) can be combined. Again, there can be two cases corresponding to action u. First, the case of action u=2 (i.e., a packet is retrieved from the queue for normal data for transmission) is considered.

$$\check{Q}_{q,q'}(u) = \begin{cases} L \otimes A_c(0), & q = q' = 0 \\ L \otimes A_c(1), & q = 0, q' = 1 \\ (L \times D(1)) \otimes A_c(0), & q = \{1, \ldots, B_c\}, q' = q - 1 \\ (L \times D(0)) \otimes A_c(0) + (L \times D(1)) \otimes A_c(1), & q = \{1, \ldots, B_c - 1\}, q' = q \\ (L \times D(0)) \otimes A_c(1), & q = \{1, \ldots, B_c - 1\}, q' = q + 1 \\ (L \times D(0)) \otimes A_c(0) + (L \otimes A_c(1)), & q = q' = B_c \\ 0, & \text{otherwise.} \end{cases} \quad (16)$$

-continued $$\check{P}_{p,p'}(u) = \begin{cases} Q(u=2) \otimes A_n(0), & p = p' = 0 \\ Q(u=2) \otimes A_n(1), & p = 0, p' = 1 \\ (Q(u=2) \times I \otimes D(1)) \otimes A_n(0), & p = \{1, \ldots, B_n\}, p' = p-1 \\ (Q(u=2) \times I \otimes D(0)) \otimes A_n(0) + \\ (Q(u=2) \times I \otimes D(1)) \otimes A_n(1), & p = \{1, \ldots, B_n-1\}, p' = p \\ (Q(u=2) \times I \otimes D(0)) \otimes A_n(1), & p = \{1, \ldots, B_n-1\}, p' = p+1 \\ (Q(u=2) \times I \otimes D(0)) \otimes A_n(0) + \\ \quad (Q(u=2) \otimes A_n(1)), & p = p' = B_n \\ 0, & \text{otherwise.} \end{cases} \quad (17)$$

Let P(u=2) denote the transition matrix for action u=2 with elements denoted by $\check{P}_{p,p'}(u)$ where the number of packets in the queue for normal data changes from p to p' for p, p'∈{0, 1, ..., $B_n$}. This can be obtained as in (17). Note that the Kronecker product of I is required to scale the size of the resulting matrix to be identical for all $\check{P}_{p,p'}(u)$. For actions u=1,3, no packet is retrieved from the queue for normal data. The derivation of transition matrix P(u=1,3) is similar to that of P(u=2). However, the departure probability matrices become D(0)=I and D(1)=0, since there is no transmitted packet. Also, Q(u=2) in (17) is replaced with either Q(u=1) or Q(u=3). The cost can be defined as a function of price paid to the network operator if a patient transmits data using an on-demand connection, and the delay incurred for critical and normal data. The immediate connection cost can be a function of state s∈Ω and action u∈$U_s$ and it can be defined as follows:

$$C_{con}(s,u) = \begin{cases} P^{wl}_{res,l}, & C = \text{reserved } WLAN \\ P^{wl}_{ond,l}, & C = \text{on-demand } WLAN \\ P^{wm}_{res,l}, & C = \text{reserved } WMAN \\ P^{wm}_{ond,l}, & C = \text{on-demand } WMAN \\ 0, & \text{otherwise} \end{cases} \quad (18)$$

for u=1,2 and L=l. The delay depends on the number of packets in the queue and arrival rate. The delay costs $C_{c,del}$ and $C_{n,del}$ for critical and normal data can be defined as follows [26]:

$$C_{c,del}(s) = \frac{X_c}{\lambda_c}, \quad C_{n,del}(s) = \frac{X_n}{\lambda_n} \quad (19)$$

where $\lambda_c$ and $\lambda_n$ are the average arrival rates of critical and normal data, respectively. These average arrival rates can be obtained from (10).

The objective function for the scheduler at the patient attached monitoring device is the expected long-term average weighted cost due to the price paid for the connections and the delay incurred. Let μ(s) denote the stationary policy (i.e., the probability of taking action u at state s). The objective function can be defined as follows:

$$J(\mu) = \lim_{t \to \infty} \sup \frac{1}{t} \sum_{t'=1}^{t} E[C(s_{t'}, \mu(s_{t'}))] \quad (20)$$

$$C(s, \mu(s)) = w_{con} C_{con}(s, u) + w_{c,del} C_{c,del}(s) + w_{n,del} C_{n,del}(s) \quad (21)$$

where $s_t$ is the state at transmission slot t, $w_{con}$, $w_{c,del}$ and $w_{n,del}$ denote the weights corresponding to connection cost, delay cost for critical and normal data, respectively. Due to the nature of biosignal data, the delay requirements are to be satisfied. An optimization problem based on CMDP can then be formulated as follows:

$$\text{Minimize } J(\mu) \quad (22)$$

$$\text{Subject to: } \lim_{t \to \infty} \sup \frac{1}{t} \sum_{t'=1}^{t} E[C_{c,del}(s_{t'}, \mu)] \le D_{c,req}$$

$$\lim_{t \to \infty} \sup \frac{1}{t} \sum_{t'=1}^{t} E[C_{n,del}(s_{t'}, \mu)] \le D_{n,req}$$

where $D_{c,req}$ and $D_{n,req}$ denote the maximum average delays measured in transmission slots.

3) Solution Approach Based on Linear Programming:

The optimal solution in terms of policy μ* for a patient-attached device can be obtained by transforming the constrained optimization formulation in (22) into linear programming (LP) [27]. Let ϕ(s,u) denote the steady-state probability corresponding to state s∈Ω and action u. An equivalent LP problem can be formulated to obtain the optimal solution of ϕ(s,u) as follows:

$$\text{Minimize } \sum_{s \in \Omega, u \in U_s} \phi(s,u) \binom{w_{con} C_{con}(s,u) +}{w_{c,del} C_{c,del}(s) + w_{n,del} C_{n,del}(s)} \quad (23)$$

$$\text{Subject to: } \sum_{s \in \Omega, u \in U_s} \phi(s,u) C_{c,del}(s,u) \le D_{c,req} \quad (24)$$

$$\sum_{s \in \Omega, u \in U_s} \phi(s,u) C_{n,del}(s,u) \le D_{n,req} \quad (25)$$

$$\sum_{u \in U_{s'}} \phi(s', u) = \sum_{s \in \Omega, u \in U_s} \phi(s,u) p(s' \mid s, u),$$

for $s' \in \Omega$ \quad (26)

$$\sum_{s \in \Omega, u \in U_s} \phi(s,u) = 1 \quad (27)$$

$$\phi(s,u) \ge 0, \forall s \in \Omega \text{ and } \forall u \in U_s \quad (28)$$

The constraints in (24) and (25) can be used to ensure that the long-term average queueing delay of critical and normal data are maintained below target levels of $D_{c,req}$ and $D_{n,req}$, respectively. The constraint in (26) can be derived from the Chapman-Kolmogorov equation. In particular, the steady-state probability of the next state s' is equal to the product of the steady-state probability of the current state s and probability of state transition p(s'|s, u) if action u is taken. Note that this state transition probability p(s'|s,u) is an element of matrix P(u) which is defined in (17). Constraints in (27) and (28) can be used to ensure that the sum of all steady-state probabilities is one, and all probabilities are non-negative, respectively. Let the optimal solution from the linear programming be denoted by $\phi^*(s,u)$. Then, an optimal policy is obtained from the probability $\theta(u,\mu^*(s))$ of using policy $u \in U_s$ in state $s \in \Omega$. This probability $\theta(u,\mu^*(s))$ can be obtained as follows:

$$\theta(u, \mu^*(s)) = \frac{\phi^*(s, u)}{\sum_{u' \in U_s} \phi^*(s, u')}, \text{ for } \sum_{u' \in U_s} \phi^*(s, u') > 0. \quad (29)$$

Note that the relationship between the SP formulation in (3)-(6) and the CMDP formulation in (22) can be based on the number of reserved connections (i.e., $x_l^{wl}$ and $x_l^{wm}$). The solution of stochastic programming affects the probabilities of a patient to use reserved and on-demand connections in WLAN and WMAN (i.e., $\rho_{c,l}^j$ and $\kappa_{c,l}^j$ where $c \in \{res,ond\}$ and $j \in \{wl,wm\}$) as shown in FIG. 1(b).

4) Implementation Based on Q-Learning:

Although the CMDP formulation above provides an optimal policy, solving the equivalent LP problem can be computationally expensive. In particular, the number of decision variables of the LP problem is $3 \times |L| K_n \times K_c \times B_n \times B_c$, where 3 indicates three possible actions, $K_n$ and $K_c$ denote the number of phases of packet arrivals for critical and normal data, respectively. The linear programming problem with the above decision variables has to be solved in an off-line manner. However, if the system parameters change dynamically over time, an on-line algorithm would be required. Therefore, an alternative method based on Q-learning is investigated which is much simpler to implement. This algorithm learns and adapts the scheduling action according to the incurred cost due to the price paid for wireless connections and due to packet transmission delays. This Q-learning algorithm is similar to the off-policy temporal difference learning method in [28]. Let Q(s,u) denote the Q-value corresponding to action u at state s. The algorithm works as follows.

1: Initialize Q(s,u)
2: loop
3: if rand( )≤e then
4: Choose action u randomly
5: else
6: Choose action u which yields the lowest Q(s,u), i.e., arg min$_u$Q(s,u)
7: end if
8: Perform action u and observe the state transition (i.e., from state s to s') and the cost $C_{con}(s,u)$, $C_{c,del}(s)$ and $C_{n,del}(s)$ due to connection cost and delays
9:

$$Q(s,u) \leftarrow Q(s,u) + \zeta((w_{con}C_{con}(s,u) + w_{c,del}C_{c,del}(s) + w_{n,del}C_{n,del}(s)) + \gamma \max_{u'} Q(s',u') - Q(s,u))$$

10: s←s'
11: end loop

In the above algorithm, e is the probability of performing explorations of the available actions. rand( )∈[0,1] is a random number generator. $\zeta$ and $\gamma$ are the weights for updating the Q-value. For numerical results, these parameters are chosen as follows: e=0.2, $\zeta$=0.5, and $\gamma$=0.4.

Note that if the value of e is large, the algorithm can frequently choose a random action, which can degrade the performance (i.e., cost becomes larger). However, if the value of e is small, the algorithm can slowly converge. The parameter $\zeta$ (i.e., learning rate) indicates the weight of updating Q-value. If the value of $\zeta$ is large, the current Q-value depends largely on the immediate received cost and the Q-value will fluctuate. As a result, the algorithm may not be stable at the steady state. However, if the value of $\zeta$ is small, the algorithm can slowly converge. The parameter $\gamma$ is the discount factor. The value of this parameter will be chosen based on the worth of cost in the future. The appropriate values of these parameters can be obtained based on simulation.

III. PERFORMANCE EVALUATION

A. Parameter Setting

In one embodiment, the service area shown in FIG. 2(a) can comprise 7 patients, and each patient can have an identical mobility model described by the following probability transition matrix:

$$T_i = \begin{bmatrix} 1-\sigma & \sigma & 0 & 0 \\ 0.0003333 & 0.9993333 & 0.0001667 & 0.0001667 \\ 0 & 0.0003333 & 0.9996667 & 0 \\ 0 & 0.0000833 & 0 & 0.9999167 \end{bmatrix} \quad (30)$$

where $\sigma$ is the probability that a patient moves from the mall to road (e.g., $\sigma$=0.0001667). In this case, the mean durations for which a patient can be at the mall, road, clinic, and home are 100, 25, 50, and 200 minutes, respectively. The prices of reserved and on-demand WLAN and WMAN connections are set as follows: $P_{res,l}^{wl}$=0.1, $P_{ond,l}^{wl}$=0.4, $P_{res,l}^{wm}$=0.2, $P_{ond,l}^{wm}$=0.6 for $l \in \{Ma, Ro\}$ (i.e., at the mall and road, respectively), and $P_{res,Cl}^{wl}$=0.05 and $P_{res,Ho}^{wl}$=0.01 at the clinic and home, respectively.

The packet arrival processes of critical and normal data are assumed to be Bernoulli. In this case, the packet arrivals are denoted by $A_c=\alpha_c$ and $A_n=\alpha_n$, where $\alpha_c$ and $\alpha_n$ denote the probabilities that the critical and normal data packets are generated in a transmission slot. The length of a transmission slot can be 1 minute. For numerical results, these packet arrival rates are assumed to be $\alpha_c$=0.1 and $\alpha_n$=0.8. The packet size for normal data is 25.6 kb and that for critical data is 5.1 kb [22]. The queue sizes for critical and normal data can be 5 and 10 packets, respectively. The successful packet transmission probabilities can be assumed to be $\beta_{res,l}^{wl}=\beta_{ond,l}^{wl}=\beta_{res,l}^{wm}=\beta_{ond,l}^{wm}$=0.98. The weights to compute the cost can be as follows: $w_{con}$=1.00, $w_{c,del}$=0.05, and $w_{n,del}$=0.03. The delay requirements of the critical and normal data can be $D_{c,req}$=2 and $D_{n,req}$=5 transmission slots, respectively. The probability of packet transmission by a patient can be approximated from the packet arrival rate as follows: $v_j \approx \min(\alpha_c+\alpha_n,1)$.

B. Numerical Results

Figure 5:
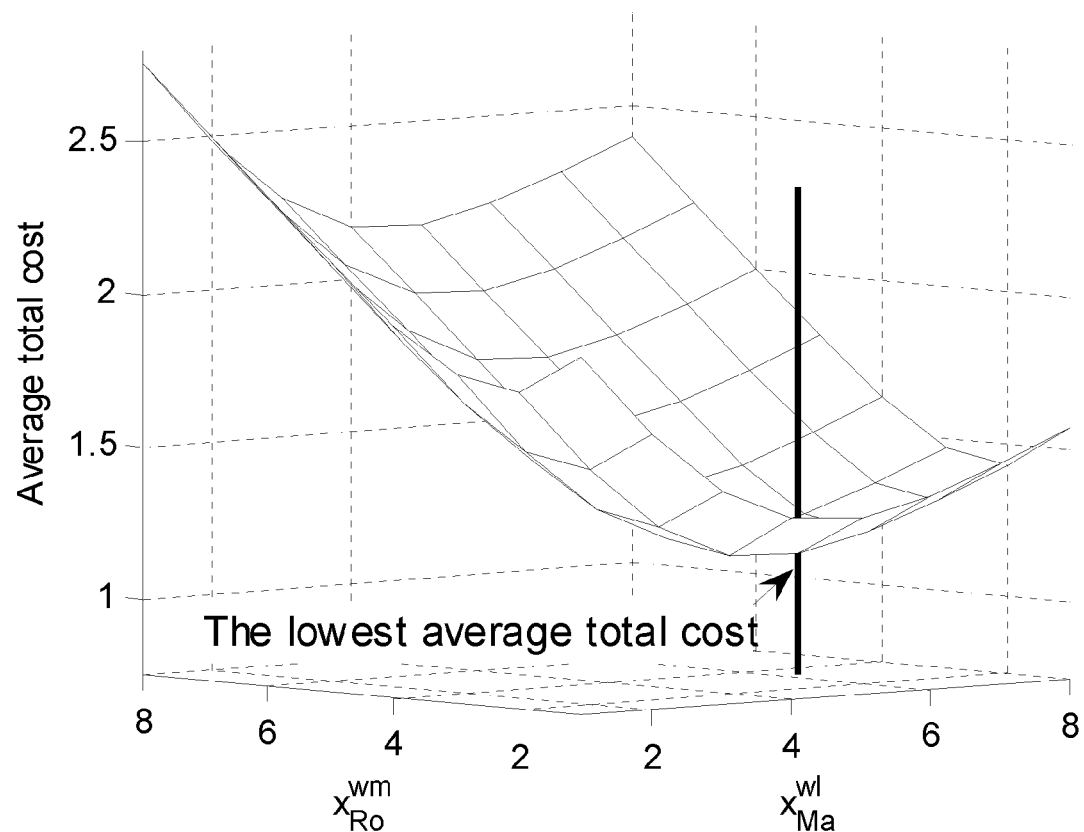
FIG. 5 is a three-dimensional graph depicting the costs of reserving connections for patients.

1) Cost of eHealth Service Provider:

FIG. 5 shows average total cost under different number of reserved WLAN and WMAN connections at the mall and on the road (i.e., $x_{Ma}^{wl}$ and $x_{Ro}^{wm}$, respectively). We observe that there can be an optimal number of reserved connections obtained from the SP formulation for which the average total cost is minimized. This is because the patients are more likely to transmit data using reserved connections and thus minimize cost since the price of a reserved connection is lower than that of an on-demand connection. Again, since the demand of the transmission from patients is random, too many reserved connections incur large cost to the eHealth service provider.

Figure 6A:
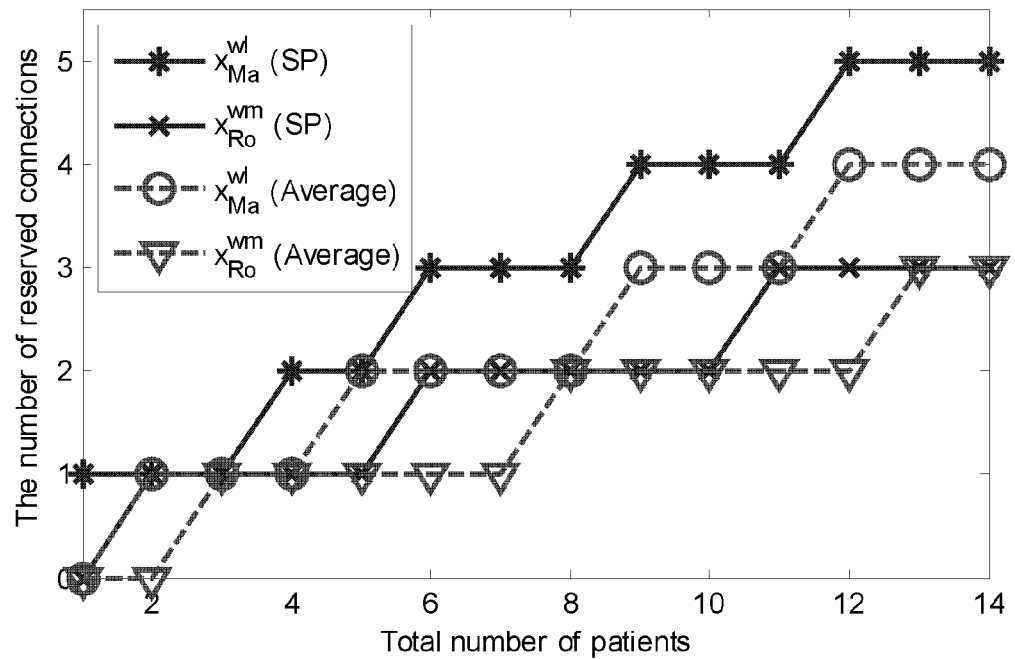
FIG. 6(a) is a two-dimensional graph depicting the number of reserved connections as compared to the total number of patients.
Figure 6B:
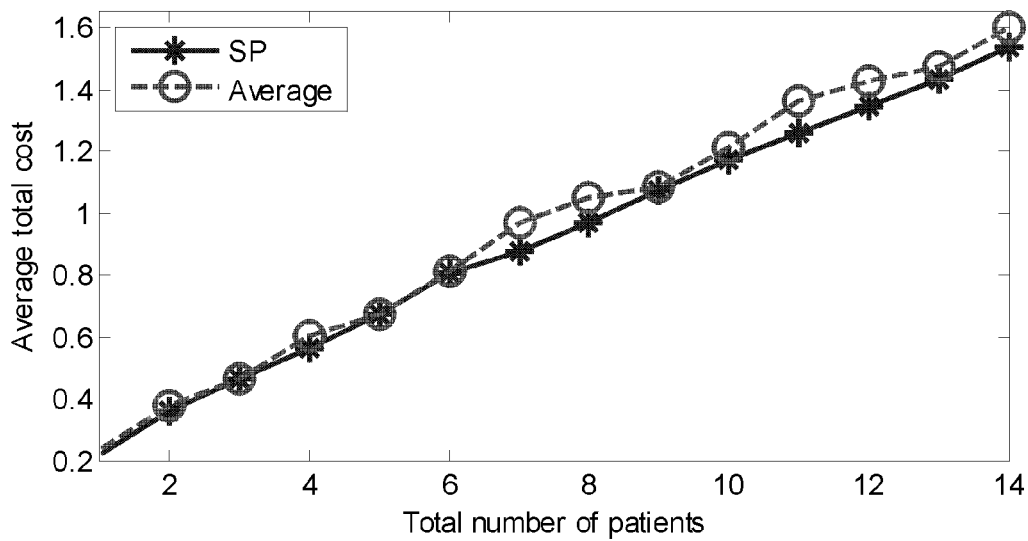
FIG. 6(b) is a two-dimensional graph depicting the average total cost as compared to the total number of patients.

Next, the number of total patients in a service area is varied. The number of reserved connections (i.e., $x_l^{wl}$, $x_l^{wm}$) obtained from solving the SP formulation, and the average number of patients transmitting packet (i.e., $\lceil \hat{n} \rceil$) are shown in FIG. 6(a). The corresponding average total costs are shown in FIG. 6(b) when the SP solution and the average number of patients are used to buy reserved connections from a network operator (i.e., denoted by legends "SP" and "Average", respectively). As expected, when the total number of patients increases, the average total cost can increase due to increasing demand for wireless connectivity. It is observed that the SP solution can be larger than that of average number of patients (FIG. 6(a)). However, the cost can be lower (FIG. 6(b)). With the SP solution, since more number of reserved connections are bought in advance, the cost incurred due to buying extra on-demand connections can be lower. Consequently, the total cost can be lower.

Figure 7:
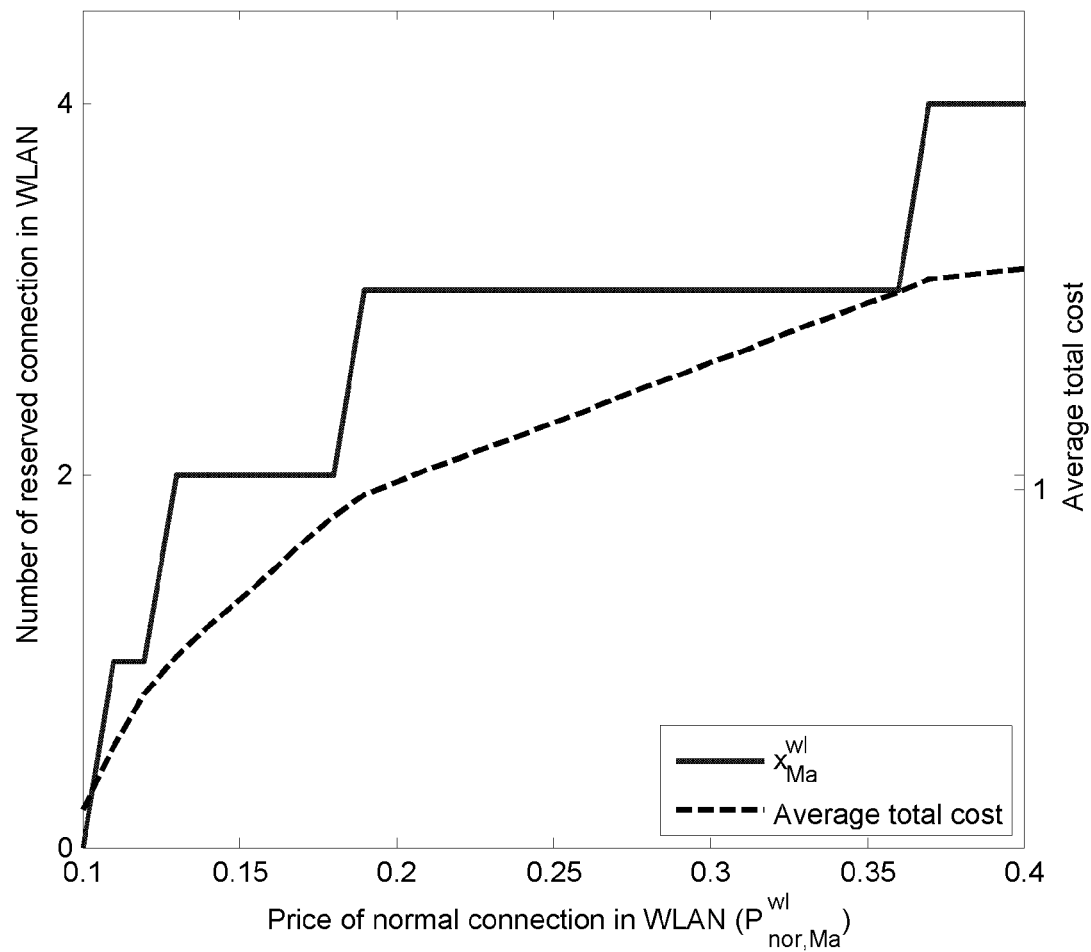
FIG. 7 is a two-dimensional graph depicting the number of reserved connections as compared to the price of normal WLAN connections.

The number of reserved connections obtained from SP and the corresponding average total costs are shown in FIG. 7 as the price of on-demand WLAN connections varies. As expected, when the price of an on-demand connection increases, the eHealth service provider can minimize the cost by buying more reserved connections. If the reserved connections are not enough to meet the demand from the patients, a higher cost will be incurred to purchase on-demand connections. The average total cost, which increases as the price increases, can be a piecewise-linear function of the price of on-demand connections.

Figure 8:
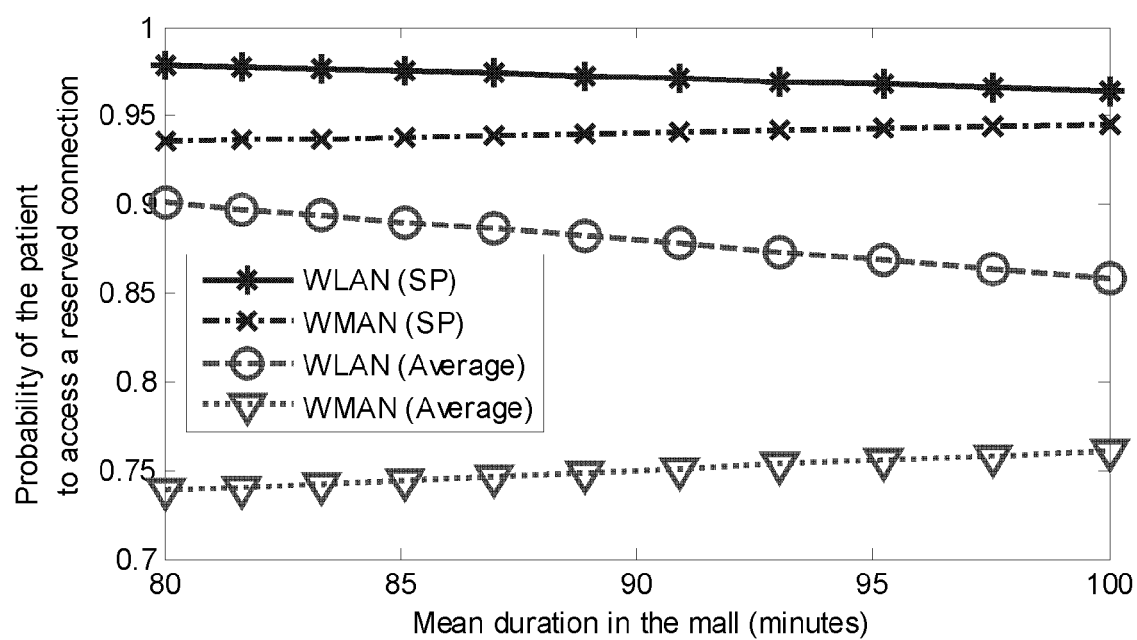
FIG. 8 is a two-dimensional graph depicting the probability of a patient to access a reserved connection.

Then, the mobility parameter for the patients (i.e., the duration of a patient to be in the mall) can be varied by adjusting σ in (30). The probabilities of a patient to access reserved WLAN and WMAN connections are shown in FIG. 8. As the duration of a patient in the mall increases, the probability of accessing reserved WLAN connections can decrease. However, the probability of accessing reserved WMAN connections increases, since more number of patients spill from WLAN to WMAN. Also, when the SP solution is compared with the average number of patients, the probabilities of accessing reserved connections obtained from the SP solution can be larger than those obtained based on the average number of patients. This result confirms the earlier observation that the cost can be lower when the SP solution is used (compared to that when the average number of patients is used for buying connections).

Figure 9A:
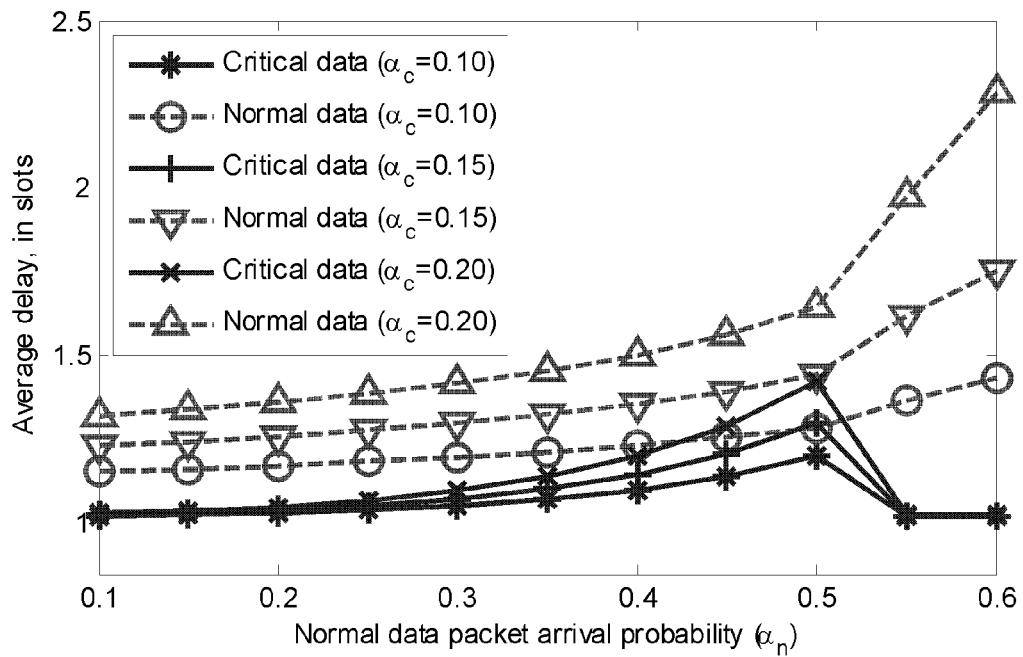
FIG. 9(a) is a two-dimensional graph depicting the average queuing delay.
Figure 9B:
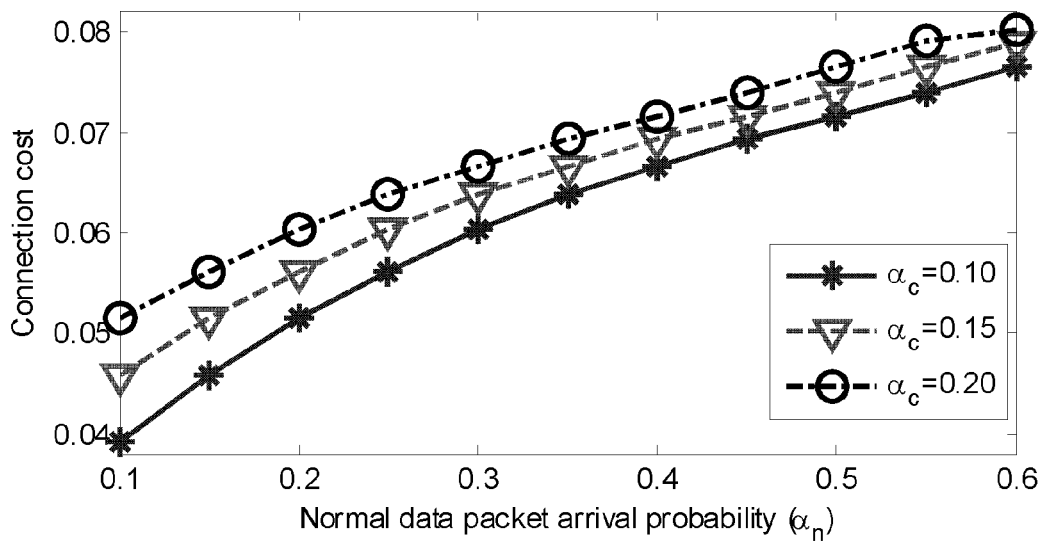
FIG. 9(b) is a two-dimensional graph depicting the connection cost as compared to the normal data packet arrival probability.

2) Scheduler Performance at the Patient-Attached Remote Monitoring Device:

The average delay and connection cost per patient are shown in FIGS. 9(a) and (b), respectively, with variations in packet arrival probabilities of both critical and normal data. In one embodiment, it is observed that the transmission delay for critical data can be smaller than that of normal data due to the different weights in the objective function defined in (21). Also, the average delay for critical data can decrease at $\alpha_n=0.5$ since the scheduling of a patient-attached device changes the action from transmitting normal data (i.e., u=2) to transmitting critical data (i.e., u=1), so that the delay for critical data can be minimized. Consequently, the delay for normal data can increase rapidly. As the packet arrival probabilities increase, the connection cost per patient can increase, since the scheduler chooses to transmit data (i.e., u=1,2) more often to reduce the average transmission delay.

Figure 10:
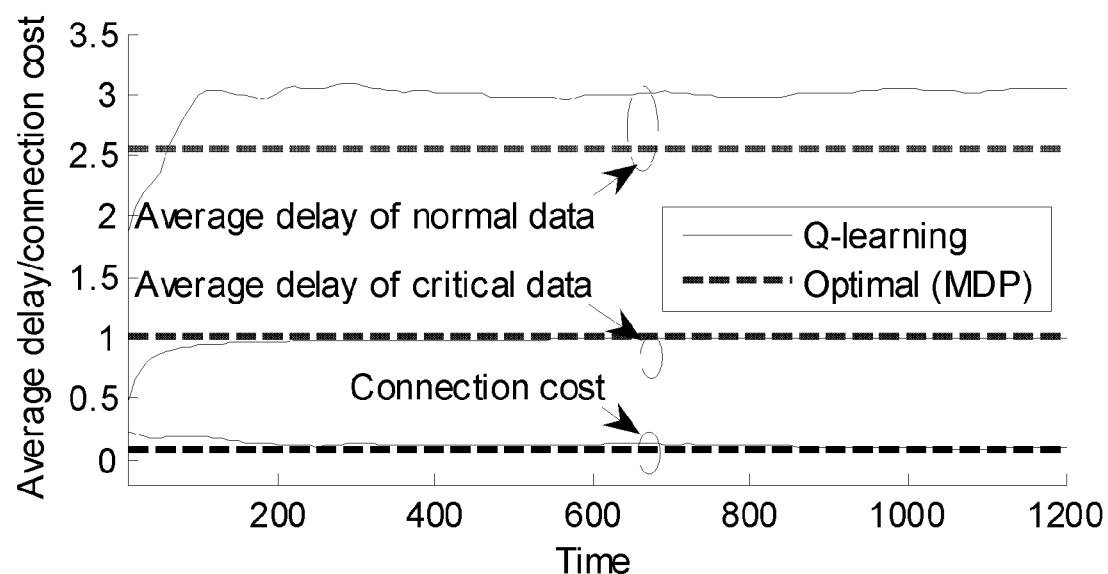
FIG. 10 is a two-dimensional graph depicting the average delay and connection costs from a Q-learning algorithm.

3) Scheduler Implementation Using Q-Learning:

FIG. 10 shows the convergence of the Q-learning algorithm. Also, the cost and delay performances of the Q-learning algorithm can be compared with those obtained from the CMDP formulation. With the Q-learning algorithm, the patient-attached device can learn and adapt its decision. Although the connection cost per patient obtained from the Q-learning is larger than that from the optimal solution, the delays for both critical and normal data can be maintained below the required limits, and the Q-learning algorithm is easy to implement. Note that the delays and connection costs from the Q-learning algorithm can be larger than those from the optimal solution, partly due to the random action selection in line 4 of the above algorithm, which is required to update the Q-value if the network state changes.

IV. CONCLUSION

An architecture for remote patient monitoring service based on heterogeneous wireless access has been presented. eHealth service providers can provide such a value-added service to mobile patients to guarantee the "always-connected" feature "anytime, anywhere". With a view to minimizing the service cost for the eHealth service provider under demand uncertainty due to the mobility of the patients, a stochastic programming problem has been formulated to obtain the optimal number of reserved connections. Also, at the patient-attached device, the transmission scheduling of biosignal data with different priority is optimized to minimize the connection cost and satisfy the delay requirements. A constrained Markov decision process formulation has been used to obtain the optimal transmission scheduling decision. The performance of the remote patient monitoring service architecture has been evaluated from different system aspects.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the scope of the invention is defined and limited only by the claims that follow.

REFERENCES

[1] P. Kall and S. W. Wallace, *Stochastic Programming*, Wiley John & Sons, January 1995.

[2] E. Altman, Constrained Markov Decision Processes: Stochastic Modeling, Chapman & Hall/CRC, March 1999.

[3] Q. Song and A. Jamalipour, "A network selection mechanism for next generation networks," in *Proc. IEEE International Conference on Communications (ICC)*, vol. 2, pp. 1418-1422, May 2005.

[4] O. Ormond, J. Murphy, and G.-M. Muntean, "Utility-based intelligent network selection in beyond 3G systems," in *Proc. IEEE International Conference on Communications (ICC)*, vol. 4, pp. 1831-1836, June 2006.

[5] W. W. Shen and Q. Q.-A. Zeng, "Cost-function-based network selection strategy in integrated wireless and mobile networks," *IEEE Trans. Veh. Technol.*, vol. 57 no. 6, pp. 3778-3788, November 2008.

[6] L.-C. Wang, A. Chen, and H.-H. Chen, "Network selection with joint vertical and horizontal handoff in heterogeneous WLAN and mobile WiMax systems," in *Proc. IEEE Vehicular Technology Conference (VTC) Spring*, pp. 794-798, April 2007.

[7] F. Bari and V. Leung, "Application of ELECTRE to network selection in a hetereogeneous wireless network environment," in *Proc. IEEE Wireless Communications and Networking Conference (WCNC)*, pp. 3810-3815, March 2007.
[8] D. Niyato and E. Hossain, "A noncooperative game-theoretic framework for radio resource management in 4G heterogeneous wireless access networks," *IEEE Trans. Mobile Computing*, vol. 7, no. 3, pp. 332-345, March 2008.
[9] K. Chebrolu and R. R. Rao, "Bandwidth aggregation for real-time applications in heterogeneous wireless networks," *IEEE Transactions on Mobile Computing*, vol. 5, no. 4, pp. 388-403, April 2006.
[10] G. T. Karetsos, S. A. Kyriazakos, E. Groustiotis, F. D. Giandomenico, and I. Mura, "A hierarchical radio resource management framework for integrating WLANs in cellular networking environments," *IEEE Wireless Communications*, vol. 12, no. 6, pp. 11-17, December 2005.
[11] F. Yu and V. Krishnamurthy, "Optimal joint session admission control in integrated WLAN and CDMA cellular networks with vertical handoff," *IEEE Transactions on Mobile Computing*, vol. 6, no. 1, pp. 126-139, January 2007.
[12] W. Song, H. Jiang, and W. Zhuang, "Performance analysis of the WLAN-first scheme in cellular/WLAN interworking," *IEEE Transactions on Wireless Communications*, vol. 6, no. 5, pp. 1932-1952, May 2007.
[13] M. Bernaschi, F. Cacace, G. Iannello, S. Za, and A. Pescape, "Seamless internetworking of WLANs and cellular networks: Architecture and performance issues in a Mobile IPv6 scenario," *IEEE Wireless Commun.*, vol. 12, no. 3, pp. 73-80, June 2005.
[14] N. Shenoy and R. Montalvo, "A framework for seamless roaming across cellular and wireless local area networks," *IEEE Wireless Commun.*, vol. 12, no. 3, pp. 50-57, June 2005.
[15] E. S.-Navarro, Y. Lin, and V. W. S. Wong, "An MDP-based vertical handoff decision algorithm for heterogeneous wireless networks," *IEEE Trans. Veh. Technol.*, vol. 57, no. 2, pp. 1243-1254, March 2008.
[16] V. S. Azhari, M. Smadi, and T. D. Todd, "Fast client-based connection recovery for soft WLAN-to-cellular vertical handoff," *IEEE Trans. Veh. Technol.*, vol. 57, no. 2, pp. 1089-1102, March 2008.
[17] B. Bernard, K. Paul, O. Juan, T. Betty, and S. Fontaine, "Telemedicine: A solution to the followup of rural trauma patients," *J. American College of Surgeons*, vol. 192, no. 4, pp. 447-452, 2001.
[18] R. Fensli, E. Gunnarson, and O. Hejlesen, "A wireless ECG system for continuous event recording and communication to a clinical alarm station," in *Proc. International Conference of IEEE Engineering in Medicine and Biology Society (IEMBS)*, vol. 1, pp. 2208-2211, September 2004.
[19] C. H. Salvador, M. P. Carrasco, M. A. G. de Mingo, A. M. Carrero, J. M. Montes, L. S. Martin, M. A. Cavero, I. F. Lozano, and J. L. Monteagudo, "Airmed-cardio: A GSM and Internet services-based system for out-of-hospital follow-up of cardiac patients," *IEEE Trans. Inform. Biomed.*, vol. 9, no. 1, pp. 73-85, March 2005.
[20] E. Guainella, E. Borcoci, M. Katz, P. Neves, M. Curado, F. Andreotti, and E. Angori, "WiMAX technology support for applications in environmental monitoring, fire prevention and telemedicine," in *Proc. IEEE Mobile WiMAX Symposium*, pp. 125-131, March 2007.
[21] D. Niyato, E. Hossain, and J. Diamond, "IEEE 802.16/WiMAX-based broadband wireless access and its application for telemedicine/eHealth services," *IEEE Wireless Commun.*, vol. 14, no. 1, pp. 72-83, February 2007.
[22] S. D. Baker and D. H. Hoglund, "Medical-grade, mission-critical wireless networks," *IEEE Eng. Med. Biol. Mag.*, vol. 27, no. 2, pp. 86-95, March-April 2008.
[23] J. C. Tejero-Calado, C. Lopez-Casado, A. Bernal-Martin, M. A. Lopez-Gomez, M. A. Romero-Romero, G. Quesada, J. Lorca, and R. Rivas, "IEEE 802.11 ECG monitoring system," in *Proc. International Conference of IEEE Engineering in Medicine and Biology Society (IEMBS)*, pp. 7139-7142, January 2006.
[24] Y.-H. Lin, I.-C. Jan, P. C.-I. Ko, Y.-Y. Chen, J.-M. Wong, and G.-J. Jan, "A wireless PDA-based physiological monitoring system for patient transport," *IEEE Trans. Inform. Technol. Biomed.*, vol. 8, no. 4, pp. 439-447, December 2004.
[25] D. Niyato E. Hossain, and J. Diamond, "Fourth generation heterogeneous wireless access networks for eHealth services: Architecture and radio resource management," Invited Chapter in *Mobile Telemedicine: A Computing and Networking Perspective*, Auerbach Publications, 2008.
[26] D. V. Djonin, A. K. Karmokar, and V. K. Bhargava, "Joint rate and power adaptation for type-I hybrid ARQ systems over correlated fading channels under different buffer-cost constraints," *IEEE Trans. Veh. Technol.*, vol. 57, no. 1, pp. 421-435, January 2008.
[27] M. L. Puterman, Markov Decision Processes: Discrete Stochastic Dynamic Programming, Wiley-Interscience, March 1994.
[28] R. S. Sutton and A. G. Barto, Reinforcement Learning: An Introduction (Adaptive Computation and Machine Learning), MIT press, 1998.

We claim:

1. A system for the remote and mobile monitoring of at least one patient, comprising:
   a heterogeneous wireless access network providing communication between at least one eHealth service provider and the at least one patient, the heterogeneous wireless access network configured to provide a number of reserved connections between the eHealth service provider and the at least one patient, wherein the number of reserved connections minimizes cost to the eHealth service provider under randomness of connection demand due to mobility of the at least one patient;
   at least one monitoring device disposed on the at least one patient, the at least one monitoring device comprising at least one sensor configured for collecting bio-signal data from the at least one patient, the at least one monitoring device further comprises a heterogeneous wireless transceiver configured to communicate the bio-signal data to the eHealth service provider over the heterogeneous wireless access network;
   wherein the bio-signal data is disposed in at least one queue comprising one or more of a group consisting of a critical data queue and a normal data queue; and
   and wherein the at least one monitoring device further comprises a scheduler configured to optimize the scheduling of the transmission of the bio-signal data by scheduling the transmission of the bio-signal data at a time when a cost of wireless access is minimized while satisfying queuing delay requirements for different bio-signal data.

2. The system as set forth in claim 1, wherein the wireless access network further comprises at least one radio access network operatively connected to the eHealth service provider for transferring received bio-signal data from the at least one patient.

3. The system as set forth in claim 2, wherein the wireless access network further comprises two or more radio access networks operatively connecting the at least one patient to the e-Health service provider.

4. The system as set forth in claim 1, wherein the scheduler is further configured to optimize the scheduling of the transmission of the bio-signal data to the eHealth service provider over the wireless access network in accordance with one or more of a group consisting of a Packet Arrival Process, a Constrained Markov Decision Process, a Solution Approach Based on Linear Programming and a Q-Learning algorithm.

5. The system as set forth in claim 1, wherein the bio-signal data comprises one or more of a group consisting of blood pressure, pulse rate, heart rate, electrocardiogram signal and sugar level.

6. A method for transmitting bio-signal data to an eHealth service provider over a heterogeneous wireless access network, the method comprising the steps of:
providing a heterogeneous wireless access network providing communication between at least one eHealth service provider and at least one patient;
determining a number of reserved connections on the heterogeneous wireless access network between the at least one eHealth service provider and the at least one patient, wherein the number of reserved connections minimizes cost to the eHealth service provider under randomness of connection demand due to mobility of the at least one patient;
providing at least one monitoring device and attaching the at least one monitoring device to the at least one patient, the at least one monitoring device having at least one sensor configured for collecting bio-signal data from the at least one patient, the bio-signal data comprising one or more of a group consisting of critical data and normal data, the at least one monitoring device further comprising a heterogeneous wireless transceiver configured to communicate the bio-signal data to the eHealth service provider over the heterogeneous wireless access network;
collecting bio-signal data from the at least one patient by the at least one monitoring device;
packetizing and buffering the collected bio-signal data into at least one queue, wherein critical data is packetized and buffered into a critical data queue and normal data is packetized and buffered into a normal data queue, the at least one queue comprising the critical data queue and the normal data queue;
optimizing the scheduling of the transmission of the queued bio-signal data by scheduling the transmission at a time when a cost of wireless access is minimized while satisfying queuing delay requirements for different bio-signal data; and
g) connecting the at least one queue to the heterogeneous wireless transceiver and transmitting the queued bio-signal data to the eHealth service provider over the heterogeneous wireless access network.

7. The method as set forth in claim 6, wherein the collected bio-signal data is transmitted to the eHealth service provider over the reserved connections.

8. The method as set forth in claim 6, further comprising the step of establishing a connection between the heterogeneous wireless transceiver and the eHealth service provider over the heterogeneous wireless access network on an on-demand basis.

9. The method as set forth in claim 6, wherein the step of optimizing the scheduling of the transmission of the bio-signal data further comprises the steps of:
determining whether or not to transmit the bio-signal data from the at least one queue;
matching the bio-signal data in the at least one queue to at least one wireless connection of the heterogeneous wireless access network; and
determining the number of packets of bio-signal data in the at least one queue.

10. The method as set forth in claim 9, further comprising the step of determining the number of reserved wireless connections available to connect to the heterogeneous wireless access network and relaying this information to a scheduler.

11. The method as set forth in claim 6, wherein the step of optimizing the scheduling the transmission of the bio-signal data is in accordance with one or more of a group consisting of a Packet Arrival Process, a Constrained Markov Decision Process, a Solution Approach Based on Linear Programming and a Q-Learning algorithm.

12. The method as set forth in claim 6, wherein the bio-signal data comprises one or more of a group consisting of blood pressure, pulse rate, heart rate, electrocardiogram signal and sugar level.

13. The method as set forth in claim 6, wherein the step of determining the optimal number of reserved connections further comprises the step of determining a probability that the at least one patient will be at a particular location in accordance with a mobility transition probability matrix.

14. The method as set forth in claim 13, further comprising the step of providing a number of reserved connections in accordance with the determined probability that the at least one patient will be at the particular location.

15. The method as set forth in claim 14, further comprising the step of providing a number of on-demand connections when the number of patients at the particular location is larger than the number of reserved connections.

16. A method for transmitting bio-signal data to an eHealth service provider over a heterogeneous wireless access network, the method comprising the steps of:
providing a heterogeneous wireless access network providing communication between at least one eHealth service provider and at least one patient;
determining a number of reserved connections on the heterogeneous wireless access network between the at least one eHealth service provider and the at least one patient, wherein the number of reserved connections minimizes cost to the eHealth service provider under randomness of connection demand due to mobility of the at least one patient;
providing at least one monitoring device and attaching the at least one monitoring device to the at least one patient, the at least one monitoring device having at least one sensor configured for collecting bio-signal data from the at least one patient, the bio-signal data comprising one or more of a group consisting of critical data and normal data, the at least one monitoring device further comprising a heterogeneous wireless transceiver configured to communicate the bio-signal data to the eHealth service provider over the heterogeneous wireless access network;
collecting bio-signal data from the at least one patient by the at least one monitoring device;
e) packetizing and buffering the collected bio-signal data into at least one queue, wherein critical data is packetized and buffered into a critical data queue and normal data is packetized and buffered into a normal data queue, the at least one queue comprising the critical data queue and the normal data queue;

optimizing the scheduling of the transmission of the queued bio-signal data by scheduling the transmission at a time when a cost of wireless access is minimized while satisfying queuing delay requirements for different bio-signal data; and connecting the at least one queue to the heterogeneous wireless transceiver and transmitting one or both of the critical data and the normal data to the eHealth service provider over the heterogeneous wireless access network.

17. The method as set forth in claim 16, wherein one or both of the collected critical data and the collected normal data is transmitted to the eHealth service provider over the reserved connections.

18. The method as set forth in claim 16, further comprising the step of establishing a connection between the heterogeneous wireless transceiver and the eHealth service provider over the heterogeneous wireless access network on an on-demand basis.

19. The method as set forth in claim 16, further comprising the step of determining whether or not to transmit one or both of the critical data and the normal data from the at least one sensor.

20. The method as set forth in claim 16, further comprising the step of optimizing the transmission of one or both of the critical data and the normal data in accordance with one or more of a group consisting of a Packet Arrival Process, a Constrained Markov Decision Process, a Solution Approach Based on Linear Programming and a Q-Learning algorithm.

21. The method as set forth in claim 16, wherein the bio-signal data comprises one or more of a group consisting of blood pressure, pulse rate, heart rate, electrocardiogram signal and sugar level.

22. The method as set forth in claim 16, wherein the step of determining the optimal number of reserved connections further comprises the step of determining a probability that the at least one patient will be at a particular location in accordance with a mobility transition probability matrix.

23. The method as set forth in claim 22, further comprising the step of providing a number of reserved connections in accordance with the determined probability that the at least one patient will be at the particular location.

24. The method as set forth in claim 23, further comprising the step of providing a number of on-demand connections when the number of patients at the particular location is larger than the number of reserved connections.

* * * * *

UNITED STATES PATENT AND TRADEMARK OFFICE
CERTIFICATE OF CORRECTION

PATENT NO. : 9,007,908 B2
APPLICATION NO. : 12/573581
DATED : April 14, 2015
INVENTOR(S) : Dusit Niyato et al.

It is certified that error appears in the above-identified patent and that said Letters Patent is hereby corrected as shown below:

In the Specification

Column 7, equation (1), the portion of the equation reading "$\otimes T_I \otimes$" should read -- $\otimes T_i \otimes$ --;

Column 7, equation (2), the portion of the equation reading "$Pr^{(\ldots, n_i, \ldots)}$" should read -- $Pr^{(\ldots, n_l, \ldots)}$ --;

Column 9, line 50, change "on-demand" to -- an on-demand --;

Column 11, equation (13), the portion of the equation reading "$[\rho_{res,l}^{wl} \quad \rho_{ond,l}^{wl} \quad \rho_{res,l}^{wm}] \quad l \in L_{wi}$" should read -- $[\rho_{res,l}^{wl} \quad \rho_{ond,l}^{wl} \quad \rho_{res,l}^{wm}], \quad l \in L_{wl}$ --;

Column 11, equation (13), the portion of the equation reading "$[\kappa_{res,l}^{wm} \quad \kappa_{ond,l}^{wm}] \quad l \in L_{wm},$" should read -- $[\kappa_{res,l}^{wm} \quad \kappa_{ond,l}^{wm}], \quad l \in L_{wm}.$ --;

Signed and Sealed this
Twenty-ninth Day of December, 2015

Michelle K. Lee
*Director of the United States Patent and Trademark Office*

CERTIFICATE OF CORRECTION (continued)
U.S. Pat. No. 9,007,908 B2

Column 12, equation (15), the portion of the equation reading

" $\begin{bmatrix} \beta_{res,l}^{wl} & \\ & \beta_{ond,l}^{wm} \end{bmatrix} \quad l = l' \in L_{wm}$ " should read -- $\begin{bmatrix} \beta_{res,l}^{wl} & \\ & \beta_{ond,l}^{wm} \end{bmatrix}, \quad l = l' \in L_{wm}$ --;

Column 12, line 40, change " $Q_{q,q'}(u)$ " to -- $\check{Q}_{q,q'}(u)$ --;

Column 13, line 1, delete "-continued";

Column 15, line 29, change " $3 \times |L| K_n \times K_c \times B_n \times B_c$ " to -- $3 \times |L| \times K_n \times K_c \times B_n \times B_c$ --;

Column 17, line 4, change " $\begin{bmatrix} \hat{n} \end{bmatrix}$ " to -- $\begin{bmatrix} \hat{n}_l \end{bmatrix}$ --; and In the Claims Column 21, claim 6, line 53, delete "g)".